United States Patent
Ntziachristos et al.

(10) Patent No.: US 8,326,406 B2
(45) Date of Patent: *Dec. 4, 2012

(54) METHOD AND SYSTEM FOR FREE SPACE OPTICAL TOMOGRAPHY OF DIFFUSE MEDIA

(75) Inventors: Vasilis Ntziachristos, Larissa (GR); Jorge Ripoll, Crete (GR)

(73) Assignee: The General Hospital Corporation, Boston, MA (US)

( * ) Notice: Subject to any disclaimer, the term of this patent is extended or adjusted under 35 U.S.C. 154(b) by 38 days.

This patent is subject to a terminal disclaimer.

(21) Appl. No.: 13/099,929

(22) Filed: May 3, 2011

(65) Prior Publication Data

US 2011/0301453 A1    Dec. 8, 2011

Related U.S. Application Data

(63) Continuation of application No. 12/632,150, filed on Dec. 7, 2009, now Pat. No. 7,962,200, which is a continuation of application No. 10/543,728, filed as application No. PCT/US2004/003229 on Feb. 5, 2004, now Pat. No. 7,647,091.

(60) Provisional application No. 60/445,016, filed on Feb. 5, 2003.

(51) Int. Cl.
*A61B 6/00* (2006.01)

(52) U.S. Cl. ..................................... 600/476

(58) Field of Classification Search .......... 600/407, 600/425, 476
See application file for complete search history.

(56) References Cited

U.S. PATENT DOCUMENTS

| | | | |
|---|---|---|---|
| 4,281,645 A | 8/1981 | Jöbsis | |
| 4,321,930 A | 3/1982 | Jöbsis et al. | |
| 4,920,491 A | 4/1990 | Eberhard et al. | |
| 5,070,455 A | 12/1991 | Singer et al. | |
| 5,090,415 A | 2/1992 | Yamashita et al. | |
| 5,391,877 A | 2/1995 | Marks | |
| 5,640,247 A | 6/1997 | Tsuchiya et al. | |
| 5,699,798 A | 12/1997 | Hochman et al. | |
| 5,762,607 A | 6/1998 | Schotland et al. | |
| 5,827,190 A | 10/1998 | Palcic et al. | |
| 5,865,754 A | 2/1999 | Sevick-Muraca et al. | |
| 6,026,319 A | 2/2000 | Hayashi | |
| 6,075,610 A | 6/2000 | Ueda et al. | |
| 6,081,322 A | 6/2000 | Barbour | |

(Continued)

FOREIGN PATENT DOCUMENTS

DE    44 45 214 A1    6/1996
(Continued)

OTHER PUBLICATIONS

Aronson;, (1995) "Boundary conditions for diffusion of light," *J. Opt. Soc. Am. A* 12, 2532-2539.

(Continued)

*Primary Examiner* — Michael Rozanski
(74) *Attorney, Agent, or Firm* — Daly, Crowley, Mofford & Durkee, LLP

(57) ABSTRACT

A method and a system for free space optical tomography provides one or more light source and one or more light sensors spaced, which in one embodiment are spaced apart from and object to be imaged. A surface capture system coupled to a variety of optical models provides the method and system with the ability to render accurate tomographic images though the light has propagated both through a diffuse medium and, in one embodiment, also through free space to the one or more light sensors.

15 Claims, 11 Drawing Sheets

U.S. PATENT DOCUMENTS

| | | |
|---|---|---|
| 6,205,347 B1 | 3/2001 | Morgan et al. |
| 6,205,353 B1 | 3/2001 | Alfano et al. |
| 6,219,279 B1 | 4/2001 | Manolescu et al. |
| 6,304,771 B1 | 10/2001 | Yodh et al. |
| 6,377,841 B1 | 4/2002 | Lin et al. |
| 6,377,842 B1 | 4/2002 | Pogue et al. |
| 6,526,309 B1 | 2/2003 | Chance |
| 6,615,063 B1 | 9/2003 | Ntziachristos et al. |
| 6,825,928 B2 | 11/2004 | Liu et al. |
| 7,383,076 B2 | 6/2008 | Ntziachristos et al. |
| 7,647,091 B2 | 1/2010 | Ntziachristos et al. |
| 7,962,200 B2 | 6/2011 | Ntziachristos et al. |
| 2004/0015062 A1 | 1/2004 | Ntziachristos et al. |
| 2004/0021771 A1 | 2/2004 | Stearns et al. |
| 2005/0149877 A1 | 7/2005 | Rice et al. |
| 2005/0283071 A1 | 12/2005 | Ripoll et al. |
| 2006/0173354 A1 | 8/2006 | Ntziachristos et al. |
| 2007/0238957 A1 | 10/2007 | Yared |
| 2008/0219933 A1 | 9/2008 | Ntziachristos |
| 2008/0312540 A1 | 12/2008 | Ntziachristos et al. |

FOREIGN PATENT DOCUMENTS

| | | |
|---|---|---|
| EP | 0 559 978 A1 | 9/1993 |
| EP | 0 329 115 B1 | 10/1993 |
| EP | 0 905 509 A1 | 3/1999 |
| EP | 1 018 747 B1 | 1/2006 |
| JP | 4122248 A | 4/1992 |
| JP | 5223738 A | 5/1996 |
| JP | 8131445 A | 5/1996 |
| JP | 11173976 A | 7/1999 |
| WO | WO 99/20997 | 4/1999 |
| WO | WO 02/41760 A2 | 5/2002 |
| WO | WO 02/41760 A3 | 5/2002 |
| WO | WO 03/102558 A1 | 12/2003 |
| WO | WO 2004/072906 A1 | 8/2004 |
| WO | WO 2009/009178 A2 | 1/2009 |
| WO | WO 2009/009178 A3 | 1/2009 |
| WO | WO 2009/055095 A1 | 4/2009 |

OTHER PUBLICATIONS

Graves et al. (2003), "A Submillimeter Resolution Fluorescence Molecular Imaging System for Small Animal Imaging," 2003 Amer. Assoc. Med. Phys. 30(5): May 2003; 901-911.

Li et al.; (1997) "Diffraction tomography for biochemical imaging with diffuse-photon density waves." *Optics Letters* 22: 573-575.

Li et al.;. (2000). "Near-field diffraction tomography with diffuse photon density waves." *Phys Rev E* 61(4 Pt B): 4295-309.

Macaskill et al.; "Iterative Approach for the Numerical Simulation of Scattering from One- and Two-Dimensional Rough Surfaces," 1993 Optical Society of America, Applied Optics, vol. 32, No. 15; May 20, 1993; pp. 2839-2847.

Markel, et al.; (2001) "Inverse problem in optical diffusion tomography. I. Fourier-Laplace inversion formulas." *J Opt Soc Am A Opt Image Sci Vis* 18(6): 1336-47.

Markel, et al.; (2001) "Inverse scattering for the diffusion equation with general boundary conditions." *Phys Rev E* 64(3 Pt 2): 035601: 1-4.

Markel et al, (2004) "Symmetries, inversion formulas, and image reconstruction for optical tomography." *Phys Rev E Stat Nonlin Soft Matter Phys* 70(5 Pt 2): 056616: 1-19.

Matson; (2002) "Diffraction Tomography for Turbid Media." *Advances in Imaging and Electron Physics* 124: 253-342.

Matson et al.; (1997) "Three-dimensional tumor localization in thick tissue with the use of diffuse photon-density waves." *Applied Optics* 36: 214-220.

Ntziachristos et al.; "Experimental Three-Dimensional Fluorescence Reconstruction of Diffuse Media by use of a Normalized Born Approximation," 2001 Optical Society of America, Optics Letters, vol. 26, No. 12; Jun. 15, 2001; pp. 893-895.

Ripoll et al.; (2005) "Experimental determination of photon propagation in highly absorbing and scattering media." *J. Opt. Soc. Am. A* 22(3):546-551.

Ripoll et al.; (2006) "From Finite to Infinite Volumes: Removal of Boundaries in Diffuse Wave Imaging", *Physical Review Letters* 96, 173903: 1-4.

Ripoll, et al.; (2003) "Iterative boundary method for diffuse optical tomography." *J. Opt. Soc. Am. A* 20(6): 1103-1110.

Ripoll, et al.; (2001) "The Kirchhoff Approximation for diffusive waves." *Phys. Rev. E* 64: 051917: 1-8.

Ripoll et al., (1999) "Scattering integral equations for diffusive waves: detection of objects buried in diffusive media in the presence of rough interfaces;"*J. Opt. Soc. Am. A* 16, 1453-1465.

Ripoll et al.; (1999) "Spatial resolution of diffuse photon density waves." *J. Opt. Soc. Am. A* 16: 1466-1476.

Schotland et al.; (2001) "Inverse scattering with diffusing waves." *J Opt Soc Am A Opt Image Sci Vis* 18(11): 2767-77.

PCT Search Report and Written Opinion for PCT/US2004/003229 mailed on Aug. 9, 2004.

U.S. Appl. No. 11/003,936, filed Dec. 3, 2004, downloaded on Aug. 13, 2009.

Ripoll et al.; "Boundary Conditions for Light Propagation in Diffusive Media with Nonscattering Regions;" Journal of the Optical Society of America; vol. 17, No. 9; Sep. 2000; pp. 1671-1681.

International Preliminary Examination Report of the ISA for PCT/US01/44764 dated Dec. 21, 2002; 3 pages.

International Search Report of the ISA for PCT/US01/44764 dated Nov. 13, 2002; 1 page.

International Preliminary Examination Report of the ISA for PCT/US03/17558 dated Jul. 8, 2005; 3 pages.

International Search Report of the ISA for PCT/US03/17558 dated Nov. 6, 2003; 3 pages.

PCT International Preliminary Report on Patentability; dated Aug. 18, 2005; for PCT Pat. App. No. PCT/US2004/003229; 7 pages.

METHOD AND SYSTEM FOR FREE SPACE OPTICAL TOMOGRAPHY OF DIFFUSE MEDIA

CROSS REFERENCE TO RELATED APPLICATIONS

This application a Continuation Application of and claims the benefit of U.S. patent application Ser. No. 12/632,150 filed Dec. 7, 2009 now U.S. Pat. No. 7,962,200, which application is a Continuation application of and claims the benefit of U.S. patent application Ser. No. 10/543,728 filed Jul. 26, 2005 now U.S. Pat. No. 7,647,091, which application claims the benefit of International Patent Application PCT/US2004/003229 filed on Feb. 5, 2004 and published in the English language as WO 2004/072906, which application claims priority from U.S. Provisional Application No. 60/445,016 filed Feb. 5, 2003 under 35 U.S.C. §119(e), which applications are hereby incorporated herein by reference in their entirety

STATEMENT REGARDING FEDERALLY SPONSORED RESEARCH

Not Applicable.

FIELD OF THE INVENTION

This invention relates generally to tomography and, more particularly, to optical tomography.

BACKGROUND OF THE INVENTION

As is known in the art, tomography is often used in construction of detailed images of internal structures of objects. Tomography relies upon a selected form of energy being directed toward and passing through the object at more than one angle. The energy from the various angles is collected and processed to provide a tomographic image. The received signals are typically less intense (i.e., darker) where the object is thicker or more dense, and more intense (i.e., brighter) where the object is thinner or less dense.

As is known, a signal received by a single energy sensor (i.e., at one angle) does not contain sufficient information to generate either a two-dimensional or a three-dimensional representation of internal structures of the object. As is also known, signals received by energy sensors arranged in a plane or volume provide sufficient information to generate a three-dimensional representation of internal structures of the object.

Tomography is used in a variety of systems with a variety of types of transmitted and received energy. For example, in x-ray Computed Axial Tomography (CAT), x-ray energy is projected through an object, typically at a variety of angles, and a variety of x-ray receivers, at a corresponding variety of angles, are used to receive the x-ray energy. A computer is used to generate an image of internal structures of the object in three dimensions from signals received by the variety of x-ray receivers. It should be recognized that x-rays tend to pass through the object in straight lines with relatively little attenuation.

One type of x-ray CAT system is used for medical imaging and the object through which the x-rays are projected is a person. However, the x-ray CAT system can be used to image internal structures of other objects, for example, luggage at an airport.

Some forms of optical tomography are known, which use one or more wavelengths of visible or invisible light rather than x-rays. However, unlike x-ray tomography, for which x-rays tend to pass through an object in a straight line with relatively little attenuation, light tends to be absorbed and to scatter when passing though an object. Therefore, light does not travel in straight lines when passing through the object. Light also tends to attenuate and to scatter more when passing though a relatively thick object having a relatively non-homogeneous medium, than it tends to attenuate and to scatter when passing through a relatively thin object having a relatively homogeneous medium.

Diffuse Optical Tomography (DOT) and Fluorescence Molecular Tomography (FMT) are known optical imaging techniques that allow optical tomography imaging of internal structure of body parts of animals and humans. DOT is an effective imaging technique capable of imaging hemoglobin concentration and oxygenation. DOT can increase the specificity in detecting disease when used in combination with more established examinations (for example for cancer or arthritis detection and characterization). In addition, DOT is used to study brain activation and to study exercising muscle.

FMT uses fluorochromes, which absorb light propagating inside of an object and emit light at a longer wavelength (lower energy) than the absorbed light inside of the object, allowing non-invasive in-vivo investigation of functional and molecular signatures in whole tissues of animals and humans. FMT enables molecular imaging, i.e., it can probe molecular abnormalities that are the basis of a disease, rather than imaging the end-anatomical effects of the molecular abnormalities as with conventional imaging approaches. Specific imaging of molecular targets provides earlier detection and characterization of a disease, as well as earlier and direct molecular assessment of treatment efficacy. FMT technology can also transfer typical in-vitro fluorescence assays, such as gene-expression profiling, elucidating cellular pathways or sensing small molecule protein interaction to in-vivo non-invasive imaging applications of large tissues.

Some conventional optical tomography systems use near infrared (near-IR or NIR) light, instead of light in the visible spectrum when passing through animal tissues, since NIR tends to attenuate less than visible light. The use of NIR light instead of light in the visible spectrum provides the ability to image deeper tissues, i.e., thicker tissues, or with higher sensitivity than in the visible light region. The development of highly efficient fluorescent probes, i.e., appropriately engineered fluorochromes with high molecular specificity emitting in the NIR, has also enabled FMT imaging of deeper tissues.

Mathematical modeling of light propagation in animal tissue and technological advancements in light sources (photon sources) and light sensors (photon receivers or photo detectors) has made optical tomography possible using diffuse light. Diffuse Optical Tomography (DOT) uses multiple projections and de-convolves the scattering effect of tissue.

Conventional DOT and FMT systems include a light source (such as a diode laser and appropriate driver), and an optical switch, which provides light to a group of optical pathways, for example, optical fibers. The optical switch directs the light source to selected ones of the optical fibers, one at a time, in a sequence. The optical fibers are in direct contact with a diffuse medium to be imaged. Using the optical fibers, the single laser source is directed to selected points on the surface of the diffuse medium. Light is collected with the use of fiber bundles, placed at multiple points, also in direct contact with the surface of the diffuse medium, and the light is directed though the fiber bundles from the diffuse medium to appropriate light sensors. A computer performs tomographic data transformations to provide images for display and storage.

Existing DOT and FMT systems employ light sources and light sensors in direct contact with the object to be imaged, providing direct contact systems. For a description of an exemplary optical tomography system, see D. J. Hawrysz and E. M. Sevick-Muraca, "Developments Toward Diagnostic Breast Cancer Imaging Using Near-Infrared Optical Measurements and Fluorescent Contrast Agents," *Neoplasia*, vol. 2, pp. 388-417, 2000.

The contact light sensors each receive light essentially from a single respective point on the surface of the object. Direct contact systems tend to reduce system versatility, limiting the shapes, sizes, and geometries of objects that can be tomograhically imaged with any particular DOT or FMT system. Direct contact systems, when used to image body parts of a patient, also tend to limit patient comfort.

Some optical tomography systems can only be used to image objects having a particular shape. For example, Wake et al., U.S. Pat. No. 6,211,512, describes an optical tomography system for use only with objects having a cylindrical geometry.

SUMMARY OF THE INVENTION

In accordance with the present invention, a system and a method to generate an image by optical tomography of internal structures of an object, such as a body part, includes a surface capture system to capture a surface model (e.g., a mathematical description) of the surface of the object and to provide the surface model to one or more optical models. The optical models can be used to account for propagation of the light toward light sensors, which can be spaced apart from the object.

In accordance with the present invention, a system for optical tomography of an object includes a data collection system to collect light having traveled through the object and in free space about the object and to generate one or more signals in response to the light. The system also includes a surface-capture system to receive surface light reflected from a surface of the object and to generate a surface model (e.g., a three-dimensional mathematical description) of at least a portion of the surface of the object. The system further includes a model processor coupled to the surface-capture system to provide one or more optical models associated with the surface of the object. A solution processor coupled to the data collection system and the model processor provides a tomographic image of the object in response to the one or more signals and to the one or more optical models. In one particular embodiment, the data collection system includes one or more light sources for emitting light directed to propagate through the object and one or more light sensors disposed to receive portions of the light which have passed through the object, wherein at least one of the one or more light sources and the one or more light sensors are disposed apart from the object.

In accordance with a still further aspect of the present invention, a method of imaging a diffuse object with optical tomography includes propagating light toward the object, capturing light, which travels through the object, and generating one or more signals in response to the light. The method also includes capturing surface light, which reflects off a surface of the object, generating a surface model (e.g., a three-dimensional mathematical description) of at least a portion of the surface of the object which reflected light, and generating one or more optical models associated with the surface of the object. The method further includes generating a tomographic image of the object in response to the one or more signals and to the one or more optical models. In one particular embodiment, the method also includes emitting light with one or more light sources, directing the light toward and through the object, and receiving the light with one or more light sensors.

With this particular technique, a method of generating a tomographic image of an object using light energy is provided by generating a mathematical description of at least a portion of the surface of the object and using the mathematical description to generate optical models. At least one of the one or more light sources and/or the light sensors can be spaced apart from the object.

BRIEF DESCRIPTION OF THE DRAWINGS

The foregoing features of the invention, as well as the invention itself may be more fully understood from the following detailed description of the drawings, in which.

DETAILED DESCRIPTION OF THE INVENTION

Figure 1:
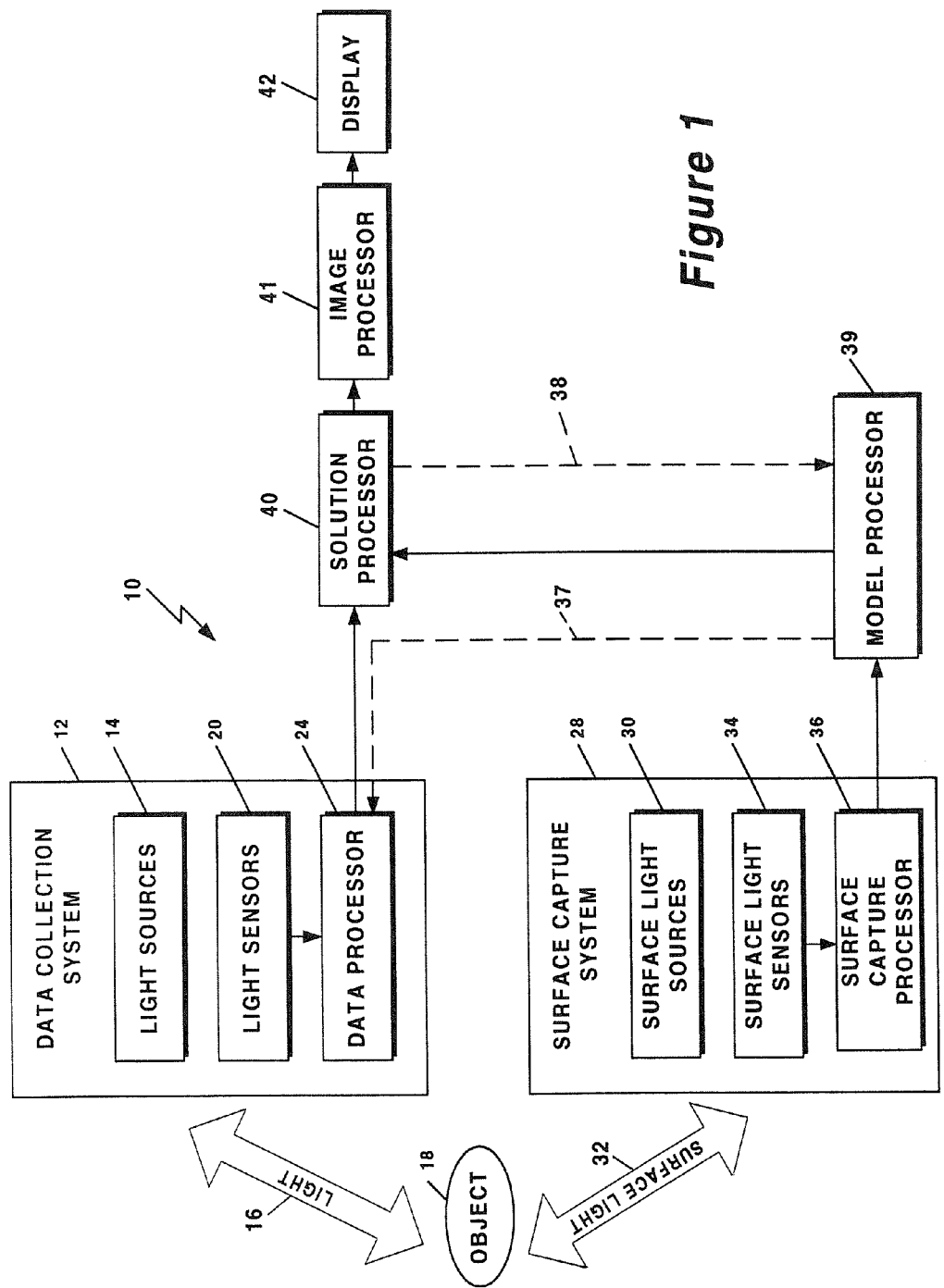
FIG. 1 is a block diagram of an exemplary optical tomography system.

Referring now to FIG. 1, an optical tomography system 10 includes a data collection system 12 having one or more light sources 14 spaced from an object 18 under test. Each of the one or more light sources 14 projects light 16 toward the object 18. Portions (not shown) of the light 16 which pass through the object 18 are received by one or more light sensors 20 which are disposed proximate, but spaced apart from, the object 18. It should be appreciated that sensors 20 are disposed about the object 20 such that the sensors 20 can receive light, which propagates through the object 18. In one particular exemplary embodiment, the light sensors 20 are disposed to be approximately one centimeter apart from the object 18, proximate a side of the object 18 which is substantially opposite from the side of the object upon which the light 16 is directed. However, in other embodiments, the one or more light sensors 20 can be disposed more that one centimeter or less than one centimeter apart from object 18, and can be disposed apart from any side of the object. In another exemplary embodiment, the light sensors are disposed to be between five and twenty-five centimeters from the surface of the object. The separation between the surface of the object and the light sensors is selected in accordance with a variety of factors, including, but not limited to, a distance that can achieve a proper focal depth, while maximizing light collection capacity.

The light sensors 20 receive the light, which passes through the object 18. Necessarily, since the one or more light sensors 14 are spaced from the object, the light propagates in free space prior to reaching the sensors 14. The one or more light sensors 20 provide corresponding light sensor signals (e.g. in the form of electrical or other types of signals) to a data processor 24. The data processor 24 digitizes, formats, and combines the digitized and formatted light sensor signals into vectors for subsequent processing, the functions of which are described in more detail in conjunction with FIGS. 4A and 5A.

In some embodiments, the light sensors 20 are also adapted to receive fluorescent light generated by fluorochromes internal to the object 18, for example from fluorescent probes injected into the object 18 which tend to coalesce in particular structures or molecules within the object 18.

The data collection system 12 is coupled to a solution processor 40 and, in the exemplary embodiment of FIG. 1, the data collection system 12 provides measured optical data to the solution processor 40 through the data processor 24. The solution processor 40 provides a solution to an "image problem" described more fully below, which provides image data corresponding to internal structures in the object 18.

The optical tomography system 10 also includes a surface capture system 28 having one or more surface light sources 30 spaced from the object 16. The one or more surface light sources 30 project surface light 32 at the object 18. Portions of the surface light 32 reflect from the surface of the object 18 and are received by one or more surface light sensors 34. The one or more surface light sensors 34 receive the surface light reflected from the object 18 and provide corresponding surface light sensor signals (e.g. in the form of electrical or other types of signals) to a surface capture processor 36. In response to the surface light sensor signals, the surface capture processor 36 generates a model (e.g., a mathematical description) of at least a portion of the surface of the object 18 from which the surface light reflects. As used herein, the term "mathematical description" can refer to an algorithmic description formed by equations, a numerical description formed by numbers, or both, and is also referred to herein as a model of the surface of the object. One surface capture system 28 generates the surface light 32 in a predetermined spatial pattern which is received by the one or more surface light sensors 34 provided as one or more three-dimensional cameras.

It will be recognized, however, that there are a variety of surface capture systems can generate a model of the surface of the object 18.

The surface capture system 28 is coupled to a model processor 39. The model processor 39 generates one or more optical models. The optical models are described more fully below. However, let it suffice here to say that, where the object 18 is diffuse to the propagation of the light 18 through the object, a first optical model generated by the model processor 39 can model the light 16 in the object 18. Furthermore, the first optical model can assume that the object 16 is not only diffuse but also that the object 16 is homogeneous vis-à-vis propagation of the light 16 within the object. In other words, the first optical model can assume that the object 16 has no internal structures. Other optical models, referred to herein collectively as a second optical model, which can be generated by the model processor 39 include, but are not limited to, a model of the light 16 as it passes from inside of the object through the surface of the object, a model of the light 16 as it propagates through free space toward the one or more light sensors 20, and a model of optical characteristics of each of the one or more light sensors 16.

In the exemplary embodiment of FIG. 1, the model processor 39 provides the one or more optical models described above to the solution processor 40. Therefore, the solution processor receives the one or more light sensor signals (e.g., electrical signals) from the data processor and the one or more optical models from the model processor.

Figure 4:
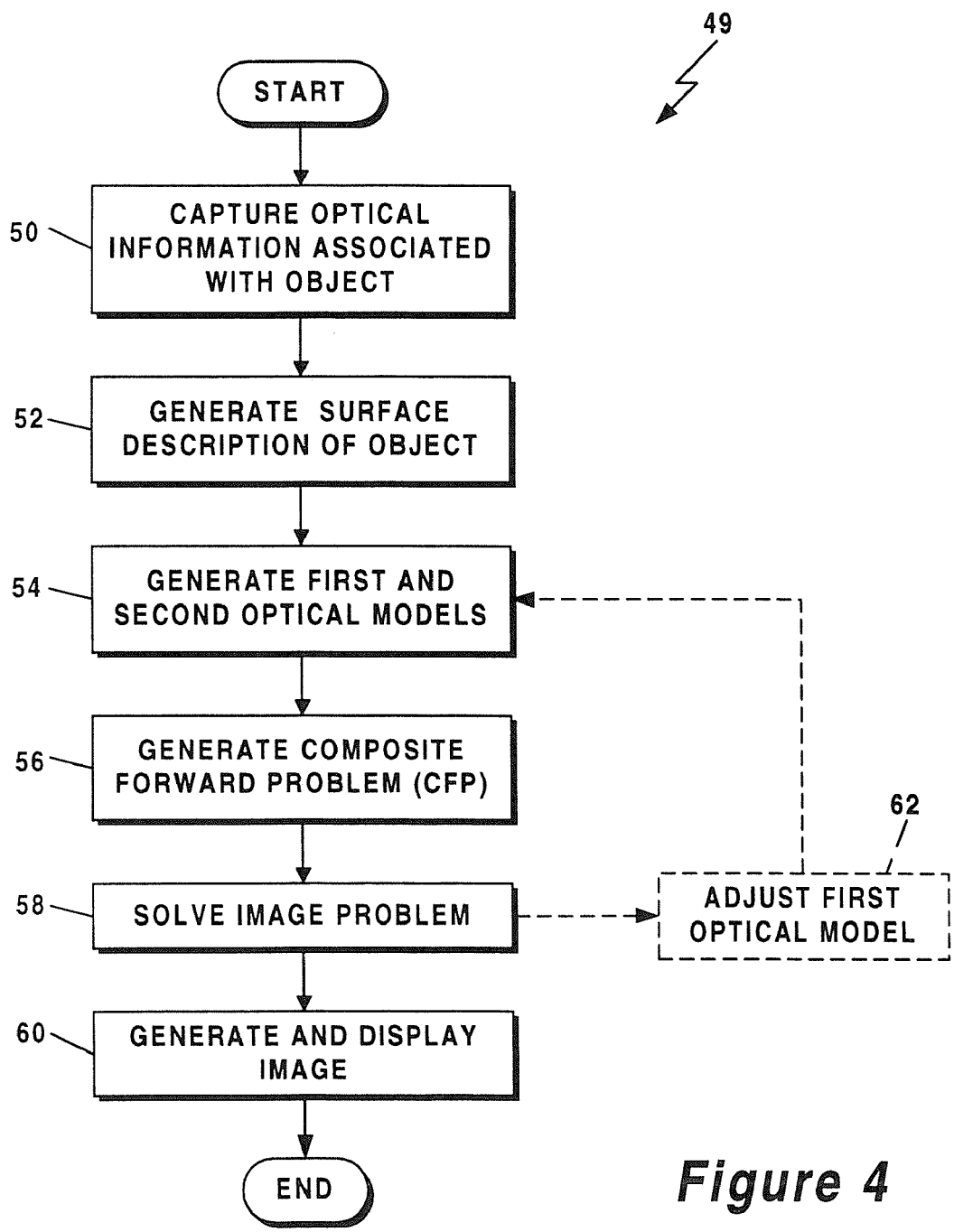
FIG. 4 is a flow chart showing an exemplary method for imaging an object with optical tomography.
Figure 4A:
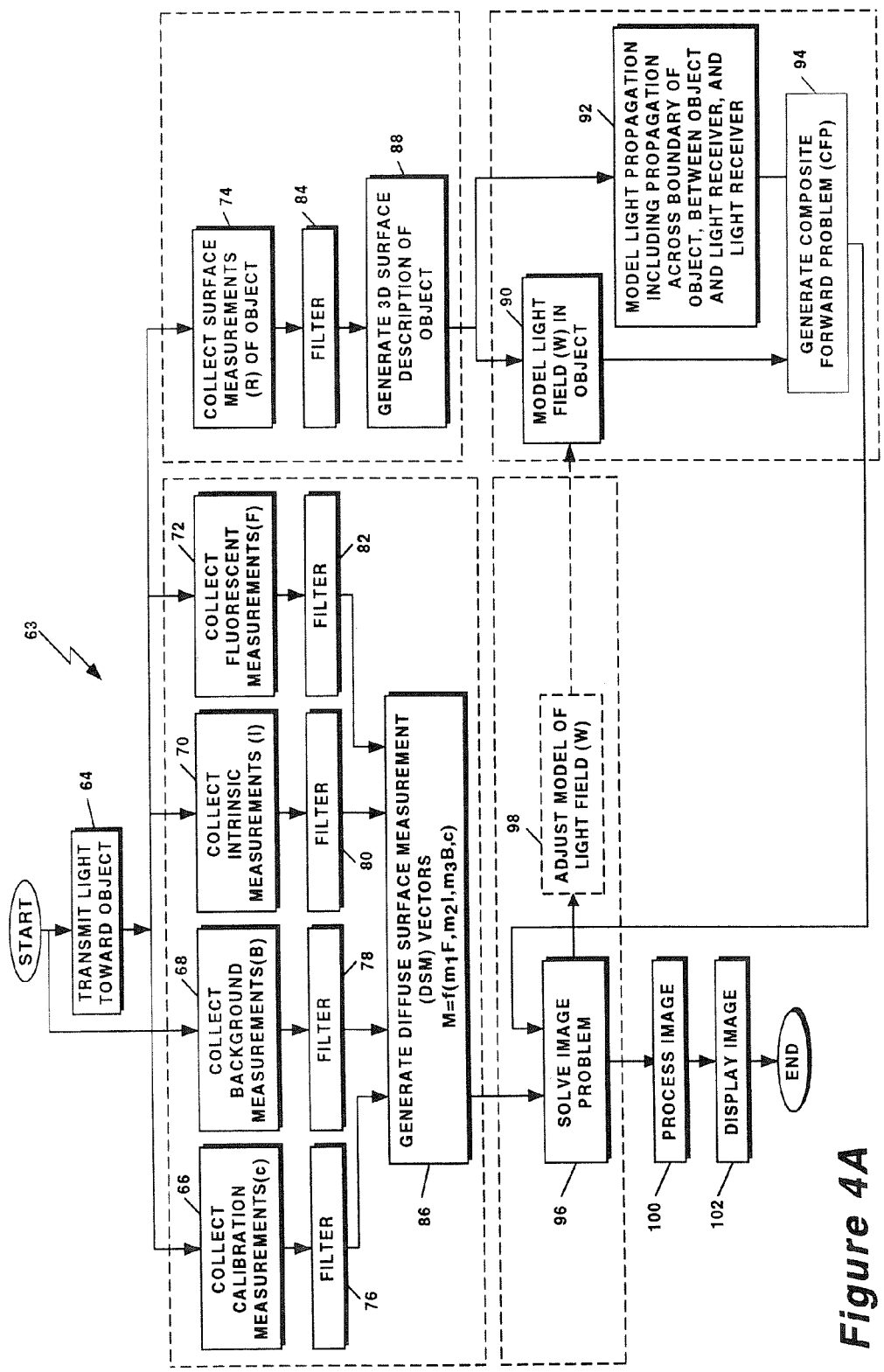
FIG. 4A is a flow chart showing further details of the method of FIG. 4.

The solution processor 40 is described more fully in conjunction with FIG. 4A. However, it should be understood that the one or more electrical signals provided by the data processor can correspond to measured optical data associated with the light 16 which has propagated through the object 18 and through free space before being collected by the one or more light sensors 20. It should be further understood that the one or more optical models provided by the model processor 39 can correspond to a theoretically derived "expected" response of the one or more light sensors 20 assuming that the object 18 is both internally diffuse and also homogeneous, e.g., having no internal structures. Where the object 18 does in fact have internal structures and is not internally homogeneous (for example, as is generally the case of a human body part), the solution processor 40 is presented with an "image problem" of the form: measurements=(theoretical predictions)×(unknown distribution), where the measurements are provided by the data collection system 12 and the theoretical predictions are provided by the surface capture system 28 in combination with the model processor 39. The solution processor 40 can solve for the unknown distribution in order to establish physical positions and characteristics of the internal structures in the object 18.

The solution processor 40 provides an output to an image processor 41, which in turn provides data to a display 42. The display 42 can provide tomographic images of the internal structures of the object 18.

As indicated by dashed line 38 in FIG. 1, in alternate embodiments, the solution processor 40 processes data and optionally can provide the data to the model processor 38. The model processor 38 can use the data from the solution processor 40 to adjust the one or more optical models provided by the model processor 39 to the solution processor 40.

Also, in alternate embodiments, as indicated by dashed line 37 in FIG. 1, data can be shared between the model processor 39 and the data collection data processor 24. The one or more optical models provided by the model processor 39 can be used to adjust the electrical signals provided by data processor 24. This alternate embodiment is described more fully in conjunction with FIGS. 5 and 5A.

It should be appreciated that the same hardware may be used to provide both the data collection system 12 and the surface capture system 28. For example, data collection light sources 14 and surface light sources 30 may be provided from the same light hardware which is controlled differently so that the light hardware provides light having different patterns (or characteristics) depending upon the intended purpose (or function) of the light hardware at a particular point in time. For example, if the light hardware were functioning as a data collection system light source 14, the light hardware would provide light having a first pattern or characteristic appropriate for the data collection system function. However, if the same light hardware were functioning as a surface capture system light source 30, the light hardware would provide light having a second pattern or characteristic appropriate for the surface capture system function. The light hardware may be provided, for example, as a programmable light source.

In one particular embodiment, the one or more light sources 14, when used in the data collection system 12, generate light in the near infrared (NIR) region and the one or more light sensors 20 are adapted to receive the light accordingly. However, in other embodiments, the one or more light sources 14 and the one or more light sensors 20 are adapted to transmit and receive light having wavelengths above or below the wavelength of NIR light, including visible light and including infrared light. In one particular embodiment, light sources 14 generate NIR light having a wavelength in the range of about 0.630 to 0.950 microns. In another particular embodiment, light sources 14 generate IR light having a wavelength in the range of about 0.950 to 2.0 microns. In another particular embodiment, light sources 14 generate visible light having a wavelength in the range of about 0.450 to 0.630 microns. The light provided by the one or more light sources 14 can be at the same wavelength or a different wavelength than the light emitted by fluorochromes described above. One of ordinary skill in the art will appreciate how to select a particular wavelength of light (or range of wavelengths) for a particular application.

In one particular embodiment, the one or more surface light sources 30 generate light in the near infrared (NIR), and the one or more surface light sensors 34 are adapted to receive the NIR light accordingly. However, in other embodiments, the surface light sources 30 and the surface light sensors 34 are adapted to transmit and receive light having wavelengths above or below the wavelength of NIR light, including visible light and including infrared light. In one particular embodiment, light sources 30 generate NIR light having a wavelength in the range of about 0.630 to 0.950 microns. In another particular embodiment, light sources 30 generate IR light having a wavelength in the range of about 0.950 to 2.0 microns. In another particular embodiment, light sources 30 generate visible light having a wavelength in the range of about 0.450 to 0.630 microns. One of ordinary skill in the art will appreciate how to select a particular wavelength of light (or range of wavelengths) for a particular application.

In another embodiment, the one or more light sources 14, when used in the data collection system 12, provide continuous wave (CW) light. However, in other embodiments, the one or more light sources 14 are modulated (e.g., in the range of Hz to kHz) or are pulsed (e.g., having pulse widths in the range of microseconds to seconds) to enable source multiplexing and/or background and ambient light separation. Corresponding light detection schemes can also be used.

In other embodiments, frequency domain sources, i.e., intensity modulated light in one or multiple frequencies (e.g., in the range of MHz to GHz) or time-domain sources, for example pulses of light having different pulse durations (for example, having pulses in the range of femtoseconds to nanoseconds) and corresponding detection systems can be used.

In still another embodiment, the one or more light sources 14 provide a planar light source, which illuminates at least a portion of the surface of the object 18. In another embodiment, the one or more light sources 14 illuminate simultaneously a plurality of spots on a surface of the object. One of ordinary skill in the art will recognize that other light patterns can be also be used.

It is understood that different projection patterns, such as those described above, may also include appropriate masks or spatial attenuation patterns (not shown) to interface to the light sensors 16, the light sensors 16 having a dynamic range pertinent to the detection system. With a mask, for example, a stray beam of light cannot directly hit and damage or saturate the light sensors 16.

Figure 2:
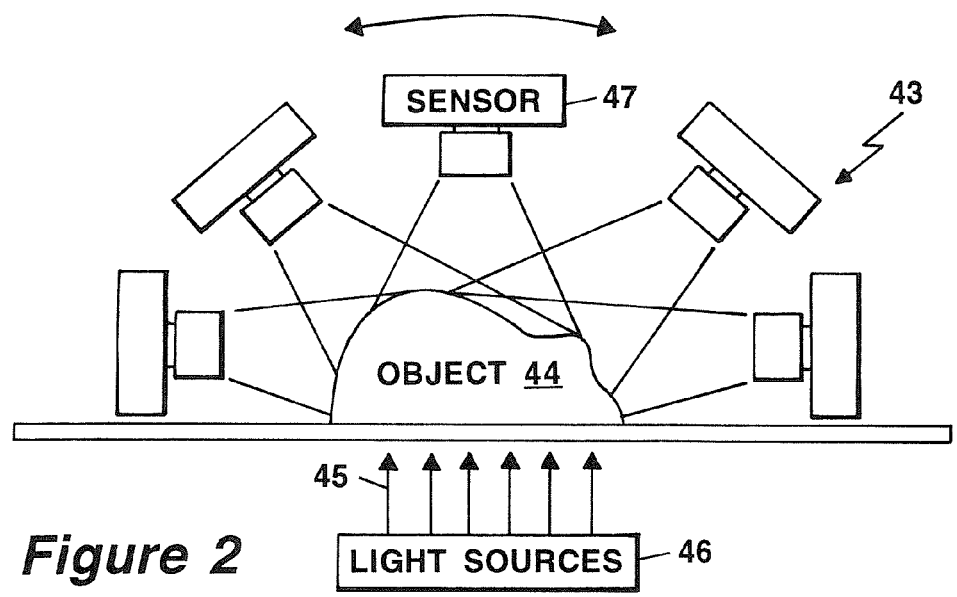
FIG. 2 is a block diagram of a portion of an exemplary optical tomography system, which includes a light sensor and a plurality of light sources.

Referring now to FIG. 2, a portion 43 of an exemplary tomography system includes one or more light sources 46 to provide light 45, which is directed at an object 44. In this particular embodiment, the one or more light sources 46 provide a plurality of light beams 45. Also in this particular embodiment, the light 45 is directed from the sources 46 toward the object from one direction. In the exemplary embodiment of FIG. 2 the light sources 46 are shown below the object. One or more light sensors 47 are disposed above the object to receive the transmitted light 45 having passed through the object 44 and from the object 44 through free space to the one or more light sensors 47. It should be appreciated that in some embodiments, the one or more light sensors 47, here shown as one light sensor 47, may be moved to a plurality of different locations as indicated by sensors 47 shown in phantom to receive the light 45. For example, the light sources 46 may direct light toward the object from above the object or beside the object in which cases the sensors 47 may be stationary or may be moved, scanning the diffuse pattern of light propagating inside the object 44 and exiting from the surface of the object 44 at different angles. In other embodiments, a plurality of different light sensors 47 may be disposed in particular locations above the object to receive the light 45. It should be appreciated that the one or more light sensors 47 can be spaced apart from a surface of the object 44.

Figure 3:
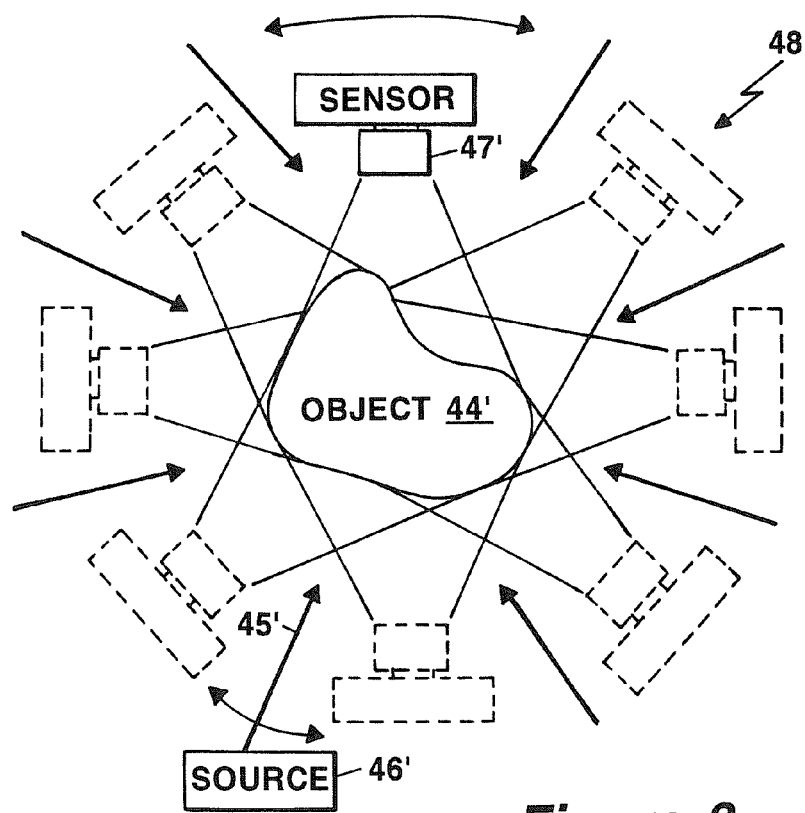
FIG. 3 is a block diagram of a portion of another exemplary optical tomography system, which includes a plurality of light sensors and a plurality of light sources.

Referring now to FIG. 3, a portion 48 of another exemplary optical tomography system includes one or more light sensors 47' and one or more light sources 46'. It should be appreciated that, in one particular embodiment, a single light source 46' can be moved to project light about all surfaces of an object 44', and that the sensors 47' are appropriately positioned to receive the light 45' having passed through the object 44' and from the object 44' through free space to the one or more light sensors 47'. In other embodiments light 45 may be provided from an array of light sources 46' and the light sensors may be provided from an array of light sensors 47'.

In still other embodiments, the light sources 46', 46 (FIG. 2) and the light sensors 47', 47 (FIG. 2) are disposed on substantially the same side of the object 44', 44 (FIG. 2). It should be apparent that the light sources 46', 46 and the light sensors can be moved or sequenced in tandem or separately. Also, in yet another embodiment, only the light sensors 47', 47 are moved or sequenced while the light sources 46', 46 remain stationary.

Figure 5:
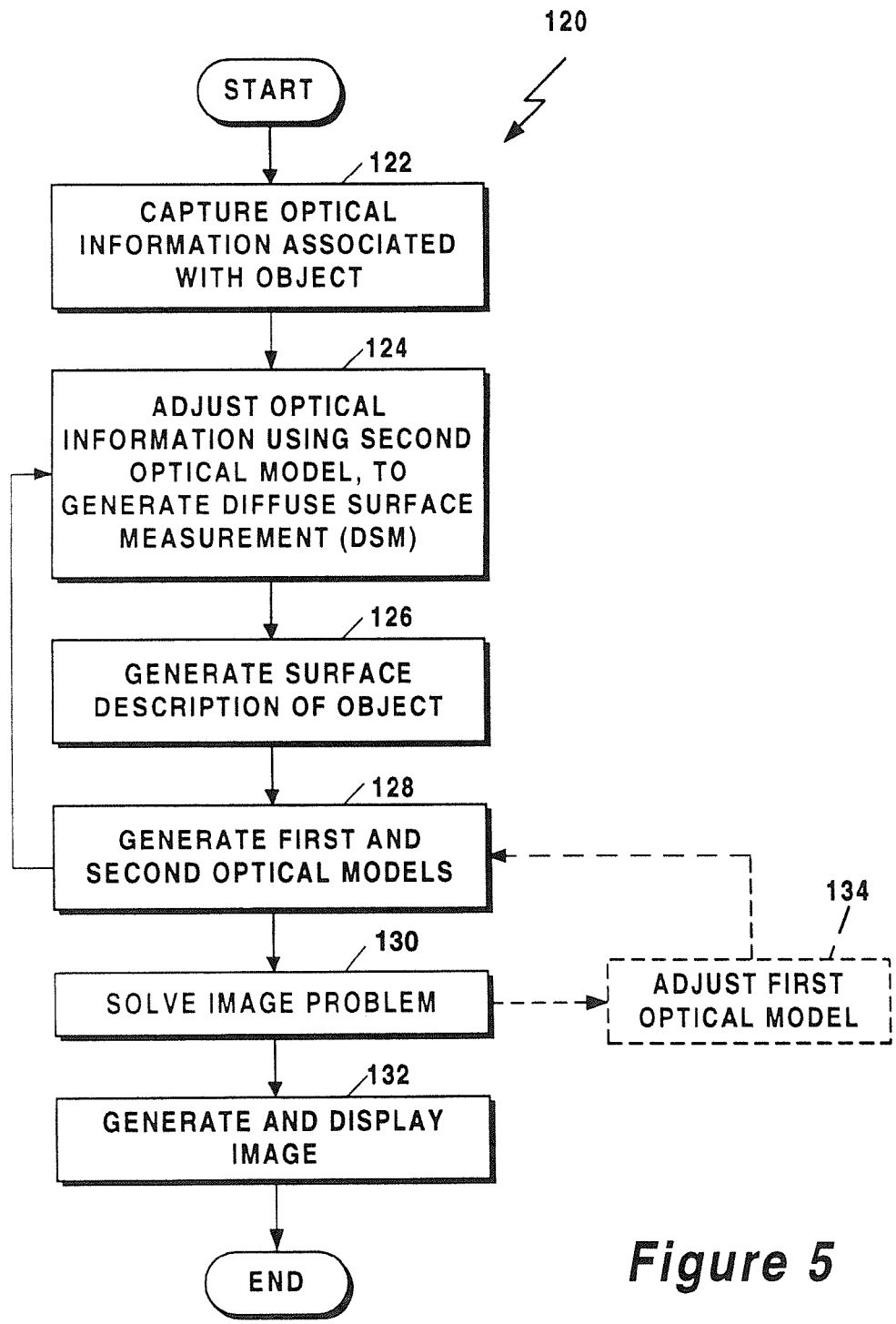
FIG. 5 is a flow chart showing another exemplary method for imaging an object with optical tomography.
Figure 5A:
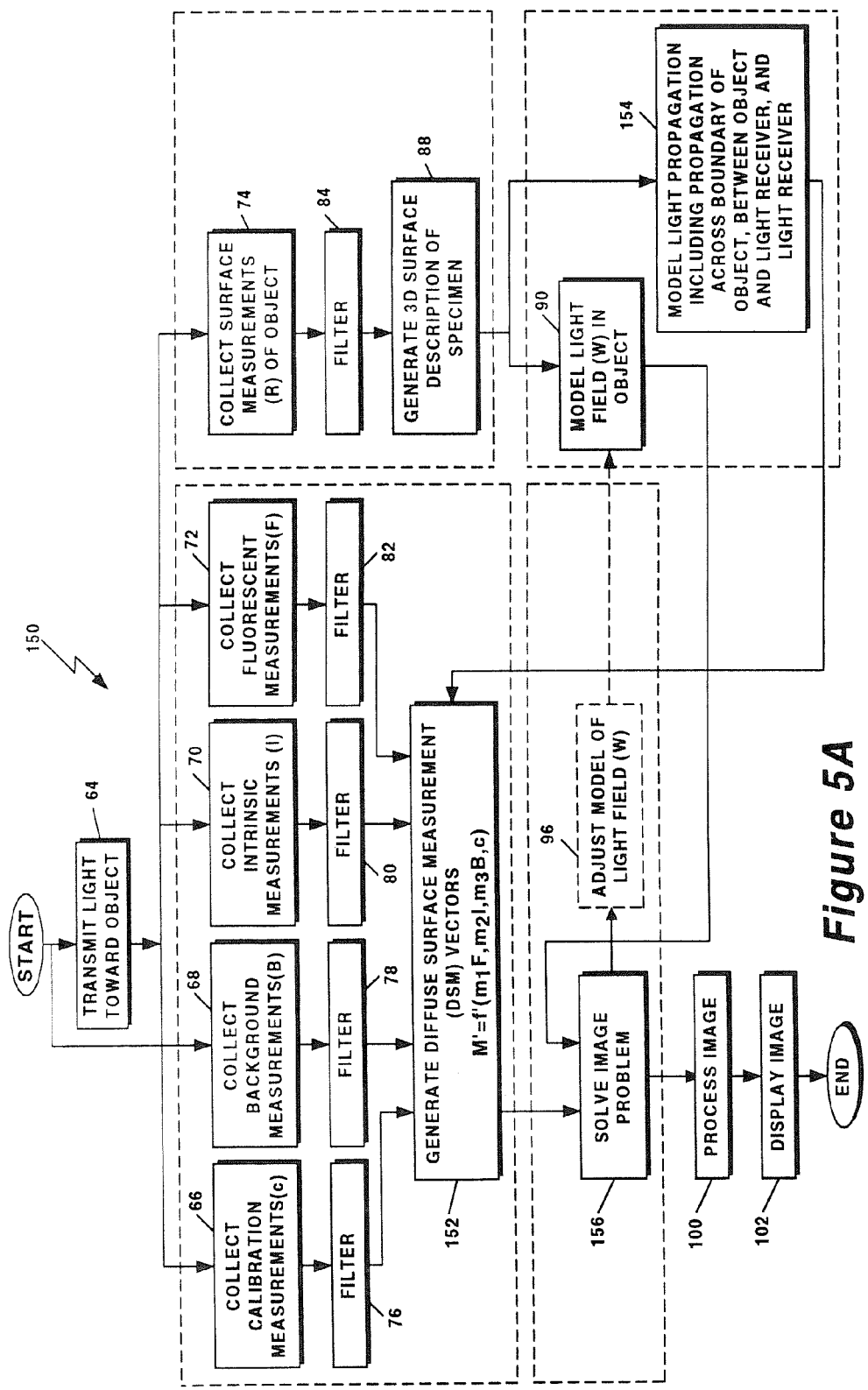
FIG. 5A is a flow chart showing further details of the method of FIG. 5.

FIGS. 4-5A are a series of flow diagrams which describe processing performed by a system, which may be similar, for example, to the system described above in conjunction with FIG. 1, having portions such as those described in conjunction with FIGS. 2 and 3. In FIGS. 4-5A, rectangular elements are herein denoted "processing blocks" and represent processor instructions or groups of instructions (e.g., computer programming code), which may be executed by a processing device (e.g., a personal computer, a general purpose computer or any other type of suitable processor). Diamond shaped elements, are herein denoted "decision blocks," and represent processor instructions or groups of instructions (e.g., computer programming code) which affect the execution of the instructions represented by the processing blocks.

Alternatively, the processing and decision blocks represent steps performed by functionally equivalent circuits such as a digital signal processor circuit or an application specific integrated circuit (ASIC). It should be appreciated that the flow diagrams do not depict the syntax of any particular programming language. Rather, the flow diagrams illustrate the functional information one of ordinary skill in the art requires to fabricate circuits or to generate computer software or other instruction sets needed to perform the processing required as described hereinbelow. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated, the steps described below are unordered meaning that, when possible, the steps can be performed in any convenient or desirable order.

Turning now to FIG. 4, a flow diagram 49, which illustrates an exemplary process to generate a tomographic image with a composite forward model (CFP) method begins as shown in processing block 50 in which optical information associated with an object, for example, the object 18 of FIG. 1, is captured. The optical information can include, for example, information provided by the light sensors 20 and the surface light sensors 34 of FIG. 1.

Processing then proceeds to processing block 52 in which a surface model (e.g., a three-dimensional mathematical description) of the surface of the object image is generated. One of ordinary skill in the art will understand that there are a variety of ways to optically generate the three-dimensional mathematical description of the surface.

First and second optical models are generated as shown in processing block 54. The first optical model describes light transmission through the object and the second optical model describes light propagation through the surface of the object, in free space about the object and characteristics of light sensors used to capture the optical information captured in processing block 50.

At processing block 56, a composite forward problem (CFP) is generated as a combination of the first and second optical models provided in processing block 54. The CFP and optical information associated with the object are used to solve an image problem as shown in processing block 58. As described above, the image problem can have the form: measurements=(theoretical predictions)×(unknown distribution), where the measurements are provided from processing block 50 and the theoretical predictions are provided by the first and second optical models at processing block 54. Solution of the image problem is further described below in conjunction with FIG. 4A.

Optionally, processing may proceed to processing block 62 in which the first optical model is adjusted and processing blocks 54-58 are repeated. Once the image problem is solved, processing flows to processing block 60 where a tomographic image is generated in displayed. Processing then ends.

Referring now to FIG. 4A, an exemplary process 63 for generating a tomographic image using a composite for a problem (CFP) approach begins by collecting a series of measurements as shown in processing blocks 66-74. In particular, calibration measurements, c, are collected in processing block 66, background measurements, B, are collected in processing block 68, intrinsic measurements, I, are collected in processing block 70, fluorescent measurements, F, are collected in processing block 72, and surface measurements, R, of the object are collected in processing block 74. While the data collected at processing blocks 66, 70, 72, and 74 is collected in the presence of light generated at processing block 64, which is directed toward the object, the background measurements collected at processing block 68 can be collected in the absence of the light generated at the processing block 64.

Calibration measurements can be collected at block 66, where the object, for example the object 18 of FIG. 1, can be replaced with an object having known characteristics. For example, the object can be replaced with an object having a homogeneous internal structure without internal structures. For another example, the object can be replaced with an object having known internal structures. The calibration measurements thus obtained can be compared later in the process 63 with tomographic images generated for the calibration object and the process 63 can be adjusted accordingly. The calibration measurements can be collected, for example, with the light sensors 20 of FIG. 1.

Background measurements can be collected in processing block 68 in order to record ambient light in the absence of the light transmitted at step 64. Background light signals, corresponding to the background light can be subtracted or otherwise cancelled from subsequent measurements in which with light is transmitted at processing block 64, including from the calibration measurements obtained at processing block 66. The background measurements can be collected, for example, with the light sensors 20 of FIG. 1.

Intrinsic measurements collected at processing block 70 can include measurements of the light that is generated at processing block 64, the light having passed through the object and having propagated in free space adjacent to the object 18. The intrinsic measurements can be collected, for example, with the light sensors 20 of FIG. 1.

Fluorescent measurements collected at processing block 72 can include measurements of fluorescent light generated by fluorochromes from within the object, such as that described in conjunction with FIG. 1. The fluorescent measurements can be collected, for example, with the light sensors 20 of FIG. 1, with or without the presence of the light transmitted at the processing block 64.

Surface measurements collected at processing block 74 can include measurements of light patterns generated at processing block 64. The surface measurements can be collected, for example, with the surface light sensors 34 of FIG. 1. However, as described above in conjunction with FIG. 1, in other embodiments, the surface measurements can be collected with the light sensors 20 of FIG. 1.

Each of the measurements collected at processing blocks 66-74 are then appropriately digitized and filtered as shown in processing blocks 76-84. The data or the information measured in processing blocks 66-72 can be used to generate composite measurement vectors, M, as shown in processing block 86, which can have the form $M = f(m_1 F, m_2 I, m_3 B, c)$, where $m_1$, $m_2$, and $m_3$ are coefficient, any of which can be zero.

Similarly, the surface measurements of the object having been appropriately digitized and filtered at processing block 84 are used to generate a surface model (e.g., a three-dimensional (3D) mathematical description) of a surface the object as shown in processing block 88. The three-dimensional surface description of the object is then used to provide a first optical model at processing block 90 as a model of a light field in an object having a shape as described by the three-dimensional surface description. The first optical model can assume an object having the shape of the actual object to be imaged, the shape provided by the three-dimensional surface description, and it can assume an object diffuse to the propagation of light like the actual object. However, as described above, the first optical model can assume that the object is homogeneous, having no internal structures.

As described above, even for a homogeneous object, light does not propagate in straight lines when passing through an object, which is diffuse to the propagation of the light. A variety of techniques are known which can provide, as the first optical model, a model of the light field in a diffuse object. For example, techniques described in PCT Application No. PCT-US03/17558 filed Jun. 4, 2003, entitled "Imaging Volumes with Arbitrary Geometries in Contact and Non-contact Tomography" can be used. Alternatively, analytical solutions of the diffusion equations based on Green's function solutions of homogeneous media, combined with first or high-order reflections from the surface elements as when using the Kirchoff approximation or the boundary element method can be used. It should be understood that while the methods described herein represent a first order approximation to the heterogeneous problem, the Green's function solutions can be updated iteratively or, can use a-priori information to represent solutions that model heterogeneous media as well.

In one embodiment, the first optical model can be calculated based on analytical methods, for example the Born or Rytov approximation. However different light field models of light in the diffuse medium based on analytical or numerical methods can also be used.

The three-dimensional surface description of the object provided at the processing block 88 is also used at processing block 92 to provide a second optical model, including, but not limited to, a model of light propagation through the boundary of the surface of the object, a model of light propagation between the object and light receiver, and a model of characteristics of the light receiver. The second optical model is further described in conjunction with FIGS. 4A and 6-7E.

The first and second optical models are then combined to generate a composite forward problem (CFP) as shown in processing block 94. It should be understood that the CFP can be used to predict the output of the light sensors, for example the light sensors 20 of FIG. 1, when the object being scanned is homogeneous and has no internal structures. However, when the tomographic imaging system 63 is used to scan an object that is not homogeneous or which has internal structures, the measurements collected at the processing block 70 will not agree with the prediction made by the CFP.

The composite forward problem and the composite measurement vectors are then used to solve the image problem as shown in block 96. As described above, the image problem can have the form: measurements=(theoretical predictions)× (unknown distribution), where the measurements are provided at processing block 86 and the theoretical predictions are provided as the CFP at processing block 94, and where the unknown distribution correspond to internal structures in the object. As described above, measurements can also be written as composite measurement vectors M=f($m_1$F, $m_2$I, $m_3$B, c), where $m_1$, $m_2$, $m_3$ are coefficients, which may take zero value.

The first optical model generated at the processing block 90 corresponds to a light field description, W. The second optical model generated at the processing block 92 corresponds to an operator, T, associated with models of the propagation of light passing through a surface of the object, propagation of the light in free space between the object and the light sensors, and characteristics of the light sensors. The three-dimensional surface description of the object generated at the processing block 88 corresponds to a description, S, of the object surface having a data set, R. The unknown distribution of optical properties described above, i.e., structures in the diffuse object, can be written as a factor, X, corresponding to the unknown distribution above. The image problem, therefore, can be written to relate M to X as M=f($m_1$F, $m_2$I, $m_3$B, c)=q(W(S), T(S), X(S)), or in the more general form as M=g(W'(S), X, S) where q, g are appropriate functions that relate the measurements to theoretical predictions and W'(S) is a forward descriptor that incorporates light propagation in diffuse and non-diffuse media. The functions q or g may be analytical or discrete. In one embodiment described below, M can be also written as M=T(S)*W(S)*X(S).

In order to solve the image problem, and in particular to solve for the unknown distribution, X, the unknown distribution, X, can be minimized, for example, by an iterative solution to the image problem. By another solution method, the function, g, can be inverted to extract the unknown distribution, X, from the set of measurements, M. Other methods can also be used.

In the CFP method 63, both T and W or W'(s) can be determined theoretically as first and second optical models at processing blocks 90 and 92, whereas measurement vectors, M, can include measured values provided at the processing clock 86. However, M, in another method, referred to as a diffuse surface measurement (DSM) method described in conjunction with FIGS. 5 and 5A, provides that measurement vectors, M, can be adjusted with theoretical predictions as well (i.e., the measurement vectors, M, are scaled by a theoretical calculated function or constant associated with an optical model). Similarly, in other embodiments, the operators T, W or W'(s), associated with the first and/or the second optical models, can be experimentally determined.

Optionally, the model of the light field may be adjusted at processing block 98 and processing blocks 90, 92, and 94 may be repeated. Once the image problem is solved at the processing block 96, processing flows to processing block 100 where the image is processed tomographically, and to processing block 102 where the tomographic image is displayed.

It should be understood that the composite measurement vectors, M, provided at processing block 86 are associated with measurements taken with a variety of relative angles between light sources and light sensors, in order to provide tomographic image processing at processing block 100.

As described above, in one embodiment, the first optical model generated at block 90 and used to calculate the light field, W, in the object can be calculated based on analytical methods, for example the Born or Rytov approximation. However, in other embodiments, the first optical model of the light field in the object can be based upon other analytical or numerical methods.

To provide the second optical model at block 92, a light source can be considered, at position, $r_s$ emitting light of wavelength, $\lambda_1$, creating an average intensity, $U_0$, within an arbitrarily shaped diffuse volume, V, of average absorption coefficient, $\mu_a$, and reduced scattering coefficient, $\mu_s'$. The normalized Born intensity U, (in either absorption/scattering or fluorescence mode) is measured by a light sensor at position $r_d \in V$, also within the volume. It is given by:

$$U(r_s, r_d) = \frac{U_1(r_s, r_d, k_1) - qU_0(r_s, r_d, k_0) - p}{U_2(r_s, r_d, k_2)} \quad (0.1)$$

$$= A_0 \cdot U_3(r_s, r_d, k_1)^{-1} \int d^3r$$

$$[U_4(r_s, r, k_1)O(r)G(r_d, r, k_2)]$$

$U_1$, $U_2$ are two diffuse photon fields measured experimentally. For example, in fluorescence tomography, $U_1$ is the fluorescence field and $U_2$ is the field measured at the excitation wavelength. In either absorption tomography or fluorescence tomography, $U_1$ and $U_2$ can be a photon field measured before and after the administration of a contrast agent respectively. Or, $U_2$ can be a calibration field measured in a calibration phantom. For different cases, the theoretically calculated fields, $U_3$ and $U_4$, can be correspondingly calculated according to an assumption that $U_1$, $U_2$ are the Green's function solutions from the source to the detector, $r_d$, or to a voxel, r, respectively. $U_o$ is a background field, which can be turned off or subtracted proportionally to the contact q. This field represents the bleed through signal in fluorescence tomography (i.e., $U_2=U_0$ and q is the bleed through contact of the filters used). Finally p is an "offset" field typically representing some offset in the data due to detection associated offsets or CD levels. The photon propagation wave numbers $k_1=(-v\mu_{a1}/D_1)^{1/2}$, $k_2=(v\mu_{a2}/D_2)^{1/2}$ are identical in absorption/scattering mode (k1=k2) and reflect the wave numbers at excitation and emission wavelengths $\lambda_1$, $\lambda_2$ respectively if fluorescence measurements are considered. The factors $\mu_{a1}$, $\mu_{a2}$, and $D_1=(3\mu_{s1}')^{-1}$, $D_2=(3\mu_{s2}')^{-1}$ are absorption coefficients and diffusion coefficients, respectively. The factor, G, is the system's Green function, which describes light propagation from a unit point source to a light sensor and can be written for homogeneous or heterogeneous media. The function O(r) is the unknown quantity reconstructed (this being the unknown scattering, absorption of fluorochrome mass) and $A_0$ is a multiplicative factor associated with system gain factors and light propagation constants such as the speed of light. The equation is actually written assuming constant or invariable (known) scattering coefficient throughout the medium but can be expanded straightforwardly to include scattering inhomogeneities as well. For simplicity, similar light propagation characteristics, e.g., $k_1 \approx k_2$ and $D_1 \approx D_2$ can be assumed, which is a valid assumption when considering the absorption scattering problem and is also a valid assumption for fluorescence measurements when there is no significant change in tissue optical properties between $\lambda_1$ and $\lambda_2$, which can be true especially for dyes in the NIR due to the relatively flat absorption spectrum of tissue in this spectral region. This approximation is done herein for simplification and the methodology works identically if different tissue optical properties are considered for $\lambda_1$ and $\lambda_2$. Furthermore, the diffusion coefficient, D, is considered to be independent of the absorption coefficient, an approximation generally valid in the NIR region.

While it is computationally very costly to calculate an accurate Green's function for arbitrary boundaries with numerical methods, the Kirchhoff approximation (KA) has been shown to be a time-efficient approach.

In a first assumption, we discretely partition a surface into N plane facets, each one having an area, $\Delta S_b$, and a surface normal, $n_b$. We further assume light sensors are at positions located outside of the object and in a non-diffusive medium (typically air) where light propagation can be modeled as straight rays instead of diffuse waves. Therefore, a transformation can be determined that describes the contribution of the surface points onto a certain light sensor, where light sensors are described as triples, e.g., $d=(r_d, n_d, A_d)$ having position, $r_d$, detector normal vector, $n_d$, and aperture, $A_d$.

In order to generate the above transformation, a variety of optical considerations are presented in FIGS. 6-7E below. However, first, the diffuse surface measurement (DSM) method described above, which also generates the first and second optical models, is further described below in conjunction with FIGS. 5 and 5A.

Referring now to FIG. 5, a flow diagram 120, which illustrates an exemplary process for generating a tomographic image with a diffuse surface measurement (DSM) technique begins as shown at processing block 122 in which optical information associated with an object, for example, the object 18 of FIG. 1, is captured. The optical information can include, for example, information provided by the light sensors 20 and the surface light sensors 34 of FIG. 1. The processing performed at block 122 can be the same as or similar to the processing performed at block 50 of FIG. 4.

Processing then proceeds to processing block 124, in which a portion of the optical information collected at block 122 is adjusted to provide altered measured data referred to herein as diffuse surface measurements (DSMs). The measured data can be altered in conjunction with the first optical model as described below.

Processing then proceeds to processing block 126, in which a surface model (e.g., a three-dimensional mathematical description) of the surface of the object image is generated. One of ordinary skill in the art will understand that there are a variety of ways to optically generate the three-dimensional mathematical description of the surface. The processing performed at block 126 can be the same as or similar to the processing performed at block 52 of FIG. 4.

The first and second optical models are generated as shown in processing block 128, the first optical model to describe light transmission through the object, and the second optical model to describe light propagation through the surface of the object, in free space about the object, and to describe characteristics of light sensors used to capture the optical information at block 122. The first optical model can be used to adjust the measured data at block 124 to provide the DSM. The first and second optical models can be the same as or similar to the optical models generated at block 54 of FIG. 4.

At processing block 130, an image problem is solved. The image problem used in the DSM method 120 can have the form: diffuse surface measurements=(theoretical predictions)×(unknown distribution), where the altered measurements are provided at processing block 124 and the theoretical predictions are provided by the first and second optical models at block 28. It should be understood that this image problem is very similar to the image problem described in conjunction with processing block 58 of FIG. 4, and can be solved using the same numerical methods. Solution of the image problem is further described above in conjunction with FIG. 4A and is not further described here.

Optionally, processing may proceed to processing block 134 in which the first optical model is adjusted in accordance with the image problem and processing blocks 128 and 130 are repeated. Once the image problem is solved, processing flows to processing block 132 where a tomographic image is generated in displayed. Processing then ends.

Referring now to FIG. 5A, in which like elements of FIG. 4A are shown having like reference designations, a DSM method is shown to have many processing blocks which are the same as or similar to processing blocks of the CFP method of FIG. 4A. Here, however, the processing blocks 152-156 can be different.

At processing block 152, diffuse surface measurements (DSM) vectors are generated, which can have the form M'=f' ($m_1$F, $m_2$I, $m_3$B, c), where $m_1$, $m_2$, and $m_3$ are coefficients. The DSM vectors are adjusted versions of the composite measurement vectors, which have the form M=f($m_1$F, $m_2$I, $m_3$B, c) generated at block 86 of FIG. 4A. From analysis above presented in conjunction with FIG. 4A, it should be understood that the composite measurement vectors represent actual measurements of light collected at blocks 66-72. It should be further understood that the composite measurement vectors are used in an image problem at block 96 of FIG. 4A in order to solve for the unknown distribution, which corresponds to internal structures in the object. In the DSM method 150 however, the image problem solved at processing block 156 receives the diffuse measurement vectors instead of the composite measurement vectors.

To provide the diffuse surface measurements at processing block 152, the second optical model 154 or portions of the second model 154 can provide model information to the processing performed at processing block 152. The model information provided for this purpose essentially moves the measurements collected at one or more of the processing blocks 66-72 by the light sensors at a reference position apart from the object to a new reference position on the object, as if the measurements had been collected by light sensors on the surface of the object. Therefore, the DSM vectors correspond to calculated measurements of the light as if the measurements had been collected by light sensors on the surface of the object.

At processing block 156 the image problem is solved, having the form: diffuse surface measurements=(theoretical predictions)×(unknown distribution). This form has the same form as that described above for the CFP method of FIGS. 4 and 4A, and can be solved using the same methods.

Figure 6:
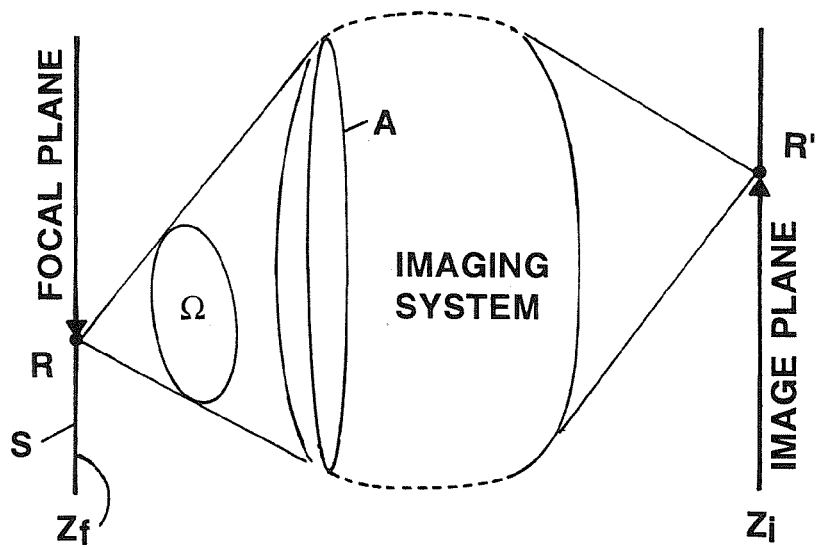
FIG. 6 is a pictorial used to describe an in-focus imaging system used in the optical tomography system of FIG. 1.

Referring now to FIG. 6, an imaging system having an aperture, A, corresponding to a solid angle, $\Omega$, generates an image point, R', of a point R lying on a surface, S. Here, the surface, S, is a planar surface lying coincident with a focal plane, $Z_f$, associated with the imaging system. The image point, R', lies on an image plane, $Z_i$, and the point, R, lies on the focal plane, $Z_f$. Assuming an ideal imaging system, which has a one-to-one correspondence between the points, R and R', for those angles that fall within an aperture, A, of the imaging system, $$F(R')|_{z=z_i} = G(R)|_{z=z_f},$$

where it is assumed that $R'|_{z=z_i} \Leftrightarrow MR|_{z=z_f}$, being a magnification factor.

The relation between the image at the point, R, that enters the aperture, A, and the image at the image point, R', is: F(R')=$\gamma$F(MR) where $\gamma$ is the overall gain factor (<1). Hereafter, the terms R and R' are sometimes used indistinctly, bearing in mind that their relationship is R'=MR. Power that goes through the imaging system is represented by:

$$P(R')|_{z=z_i} = \gamma P(MR)|_{z=z_f} \quad (0.2)$$

Therefore, we will concentrate on the measurements at the point, R. The "stop," (for example, f-stop in conventional photography) of the imaging system is defined by the smallest aperture at an entrance to the imaging system. The aperture, A, having an area also denoted as A, delimits the angle of acceptance of the imaging system.

Figure 6A:
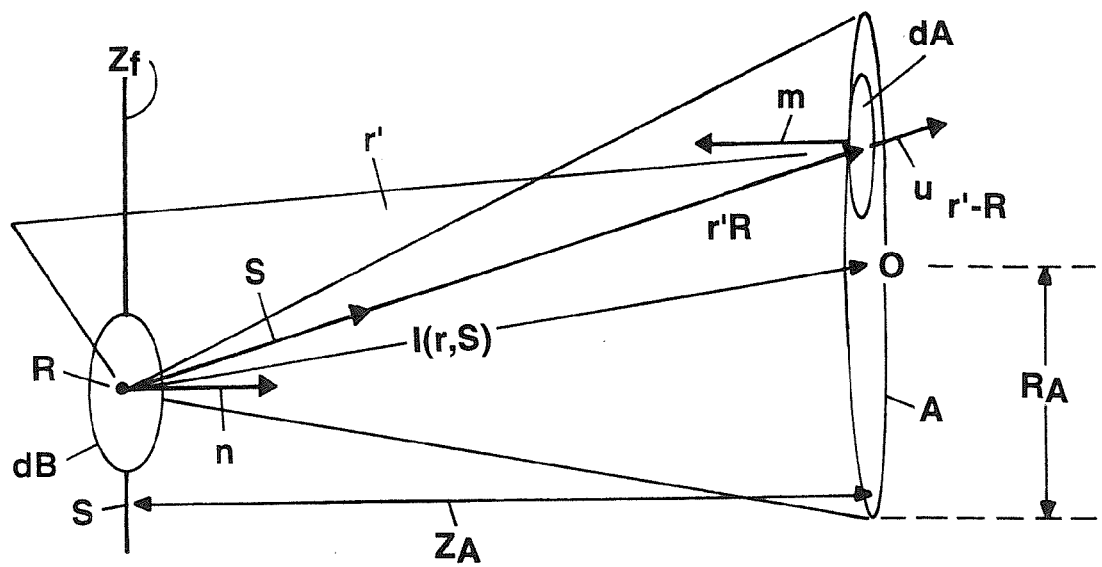
FIG. 6A is another pictorial used to describe the in-focus imaging system used in the optical tomography system of FIG. 1.

Referring now to FIG. 6A, in which like elements of FIG. 6 are shown having like reference designations, the plane, S, having the point R, again is coincident with the focal plane, $Z_f$, of the imaging system. Therefore, the point, R is in focus in the imaging system (FIG. 6). Here, however, the image plane, $Z_i$, of FIG. 6 is not explicitly shown. Instead, the aperture, A, corresponds to an aperture provided within the imaging system of FIG. 6, and in front of (to the left of) the image plane of FIG. 6.

As described above, the planar surface, S, is located exactly at the focal plane, $Z_f$. The planar surface, S, includes a differential surface area, dB, about the point, R. The differential surface area, dB, is shown having a differential surface normal, n. The differential surface area, dB, about the point, R, is associated with a differential surface area, dA, at the aperture, A. The differential surface area, dA, is shown having a differential surface normal, m. A distance, $Z_A$, corresponds to a distance from the focal plane, $Z_f$, to the aperture, A. The differential surface area, dB, is also shown having a vector, s, in a direction of the differential surface area, dA, and the differential surface area, dA, is shown having a vector, $u_{r'-R}$, in a parallel direction, each corresponding to an intensity of light passing through the respective differential surface area. The aperture, A, can be off-axis with respect to the differential surface normal, n, or it can be on-axis. A vector, r', represents a point corresponding to the point, R, but at the differential surface area dA. A vector, O, represents the center of the aperture having area, A.

A total power measured at the image point, R' (FIG. 6), due to the differential surface area, dB, is equivalent to the total power, P, at the point, R, (for example, in Watts) irradiated into the solid angle, $\Omega$ (FIG. 6):

$$P(R) = \int_\Omega I(r, s) n \cdot s \, dB \, d\Omega, \quad \forall s \in \Omega \quad (0.3)$$

where the vector, n, is the differential surface normal to the differential surface area dB, and I(r,s) represents the amount of power that at point r flows within a certain solid angle defined by unit vector s for each existing wavelength. I(r,s) is commonly referred to as the specific intensity. I(r,s) is shown in FIG. 6A.

Due to the relationship between r' and the point, R, the differential surface area, dB, may be seen as a "detector area" at the image plane (FIG. 6). In other words, the differential surface area, dB, represents an image of the detector area at the focal plane, $Z_f$. The solid angle, $\Omega$, (FIG. 6) corresponds to the aperture, A, (i.e., the entrance pupil, lens, etc.) and to the point, R. In order to solve Equation (0.3) it is most convenient to write this solid angle, $\Omega$, in terms of the differential surface area, dA, at the aperture, A, as:

$$d\Omega = \frac{m \cdot u_{R-r'}}{|r' - R|^2} dA \quad (0.4)$$

where m is the differential surface normal at the aperture, A, and where $$u_{r'\cdot R} = (r'-R)/|r'-R|,$$

where r' is the vector that defines a point in the aperture, A. By using equation (0.4), the total power radiated by the differential surface area, dB, is:

$$P(R) = \int_A I(R, u_{r'-R})(n \cdot u_{r'-R}) \frac{(m \cdot u_{R-r'})}{|r' - R|^2} dB dA, \quad (0.5)$$

where the integration is performed over the area of the aperture, A.

If the aperture, A, has a radius, $R_A$, then:

$$dA = 2\pi R_A dR_A \text{ and}$$

$$|r'| = \sqrt{Z_A^2 + R_A^2},$$

where $Z_A$ is a distance from the focal plane ($Z_f$) to the aperture, A.

Equation (0.5) represents the exact solution within the Radiative Transfer formulation for the power, P(R'), (by using Equation (0.2)) measured by a light sensor corresponding to the differential surface area, dB', (dB'≲M²dB), where the prime symbol indicates that the differential surface area dB is the detector area measures at the imaging plane.

Using the above equations, in conjunction with FIG. 6B below, two case are considered: a) when the area of the aperture is small ($Z_A \gg R_A$), and b) when the area of the aperture is very large ($Z_A \ll R_A$). Below, in conjunction with FIG. 6C, an isotropic light source is considered.

Figure 6B:
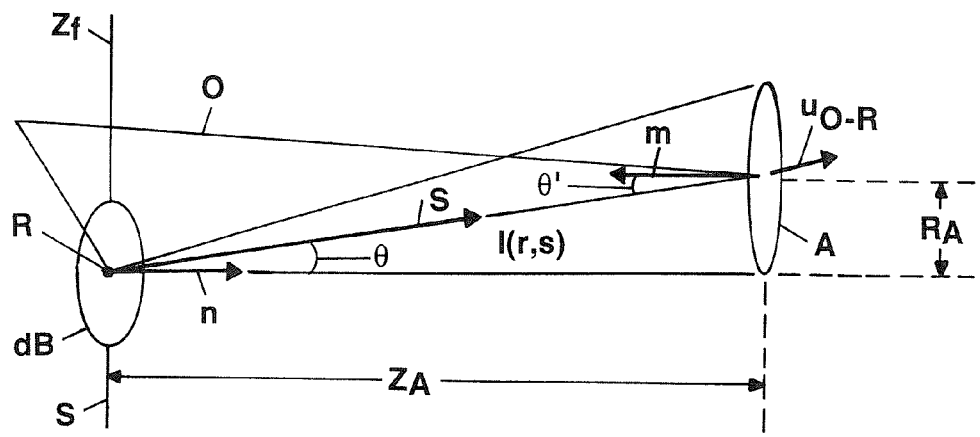
FIG. 6B is a pictorial used to describe the in-focus imaging system having a small aperture and having a large aperture used in the optical tomography system of FIG. 1.

Referring now to FIG. 6B, in which like elements of FIGS. 6 and 6A are shown having like reference designations, a small aperture, A, is shown, where the vector, O, represents a center of the aperture, A. Again, the point, R, is in focus in the imaging system (FIG. 6).

For a small aperture, A, where $Z_A \gg R_A$, the angular dependence in the integral of Equation (0.5) may be approximated to be a constant, yielding:

$$P(R) = I(R, u_{O-R}) \cos\theta \frac{\cos\theta'}{|O-R|^2} A dB \quad (0.6)$$

where O is the vector that represents the center of the aperture, A, and where, $$\cos\theta = n \cdot u_{O-R}, \cos\theta' = m \cdot u_{R-O},$$

where θ is the angle between the normal, n, of the differential surface area, dB, and the unit vector pointing from O towards R, and θ' is the angle between the surface normal, m, of aperture area, A, and the unit vector pointing from R towards O.

The above approximation is equivalent, for example, to a light fiber having the aperture, A, and surface normal, m, located a distance, O–R, from a radiating source. As an example, the case can be considered in which the surface normals, m and n, are parallel (as in the case when a planar surface is imaged), and where the differential surface area, dB, radiates as a Lambertian source, $I(R,s) = I_0(R)$. In this case the power measured at the point, R, is:

$$P(R) = I_0(R) \cos^2\theta \frac{A}{r^2} dB \quad (0.7)$$

where r=|r–O| is the distance between the points defined by r and O.

For a large aperture, where $Z_A \ll R_A$, most or all light flux that leaves the differential surface area dB will be detected. That is, the detected power at the point, R' (FIG. 6), is equal to the total power emitted from the differential surface area, dB, and:

$$P(R) = \int_{(2\pi)^+} I(R, s)(n \cdot s) dB d\Omega = J_n^+(R) dB \quad (0.8)$$

where $J_n^+$ is the total flux [e.g., in Watts/cm²] that traverses the differential surface area, dB, from right to left as shown.

It should be appreciated that Equation (0.8) is general for any angular dependence of light radiated from the image plane, i.e., from the surface, S. For a large aperture, no angular dependence introduced due to geometrical considerations is expected in the image plane as long as the surface normals, m and n, are parallel. Also, for a large aperture, the in focal plane, $Z_f$, may be seen as a collection of virtual light sensors (e.g., optical fibers) each having a differential surface area, dB, and each in contact with the surface, S. In the case where the surface normals, m and n, are not parallel, the solid angle integral of the above equation will not be in the whole hemisphere $(2\pi)^+$ and an angular dependence will appear.

Figure 6C:
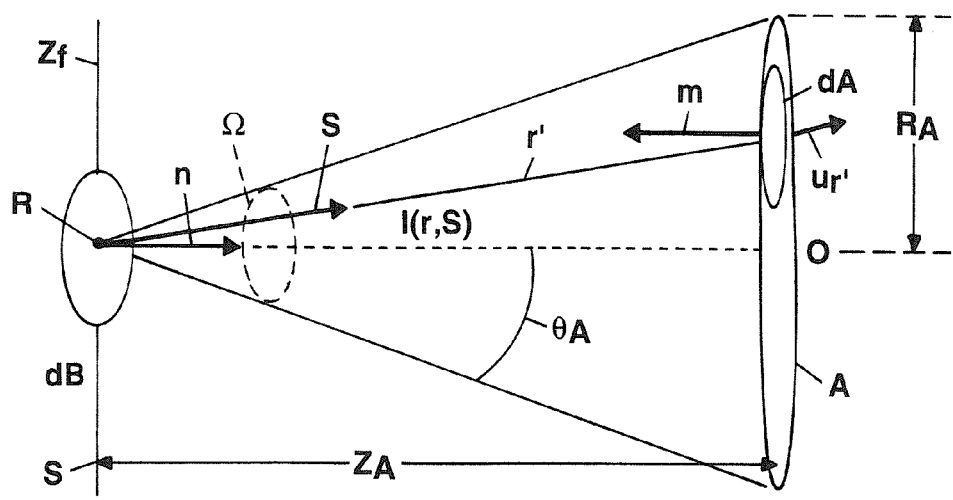
FIG. 6C is a pictorial used to describe an isotropic light source used in the optical tomography system of FIG. 1.

Referring now to FIG. 6C, in which like elements of FIGS. 6-6B are shown having like reference designations, again, the point, R, is in focus in the imaging system (FIG. 6).

In order to understand more clearly the expressions derived above in conjunction with FIG. 6B obtained for large and small apertures, a special case is shown and considered where an arbitrary aperture, A, is on-axis with the differential surface area, dB. In this case, the total detected power is equivalent to:

$$P(r) = 2\pi \int_\Omega I(r, s) \cos\theta \, dB \, d(\cos\theta) \quad (0.9)$$

where the solid angle, Ω, (FIG. 6) is represented by $d\Omega = d\phi \sin\theta d\theta$. The limits of integration are $\cos\theta \in \{\cos\theta_A, 1\}$, where $\cos\theta_A = Z_A/\sqrt{Z_A^2 + R_A^2}$. Assuming an isotropic source, $I(r,s) = I_0$, Equation (0.9) can be solved to give:

$$P(r) = \pi I_0 dB (1 - \cos^2\theta_A) \quad (0.10)$$

and therefore, $$P(r) = \pi I_0 dB \frac{R_A^2}{Z_A^2 + R_A^2} \quad (0.11)$$

When dealing with the Lambertian approximation, it is shown above that the total outward flux (i.e., from right to left), $J_n^+$, is related to the specific intensity as $I_0 = J_n^+/\pi$. Therefore, it should be recognized that when $Z_A \ll R_A$, equation (0.11) is equivalent to equation (0.8). Also, since an area, A, of the aperture, A, is $A = \pi R_A^2$, equation (0.11) can be written as $P(r) = I_0 A dB/(Z_A^2 + R_A^2)$. In the case where $Z_A \gg R_A$ this reduces to $P(r) \approx I_0 A dB/Z_A^2$, thus recovering Equation (0.7) for the on-axis case.

Figure 7:
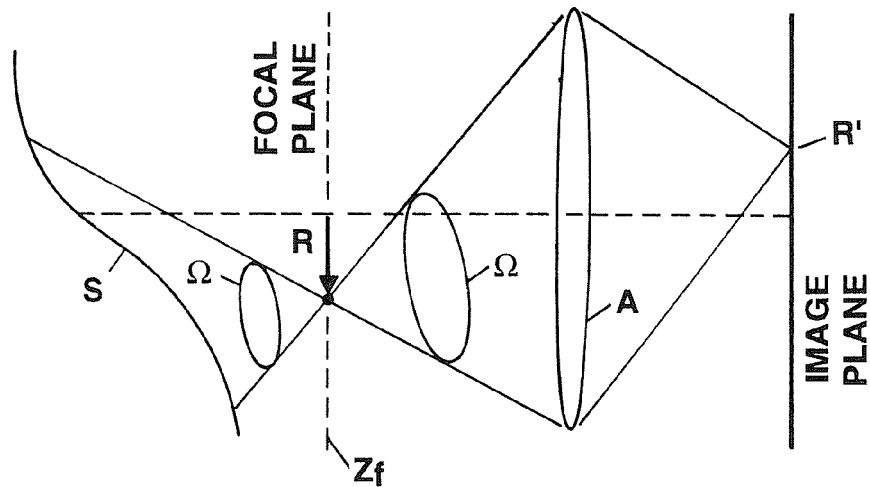
FIG. 7 is a pictorial used to describe an out-of-focus surface contribution received by a light sensor used in the optical tomography system of FIG. 1.
Figure 7A:
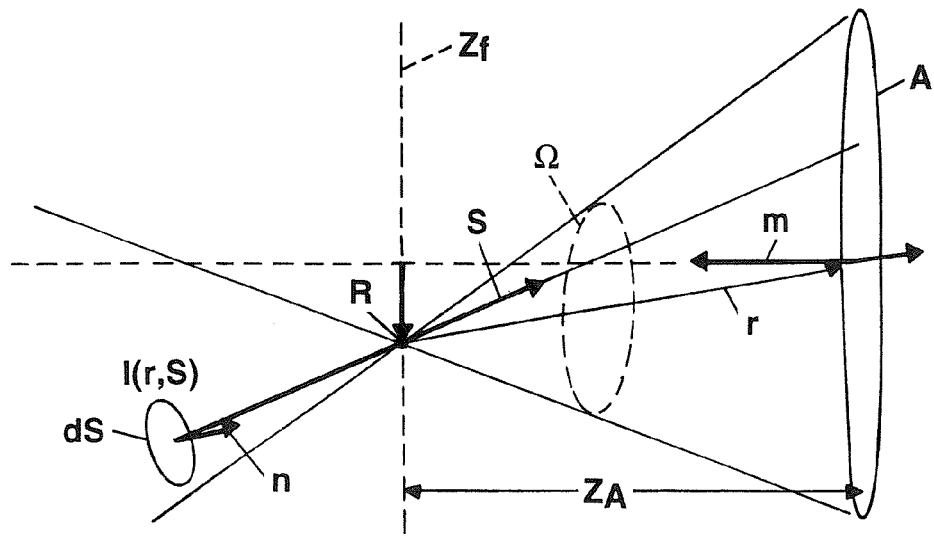
FIG. 7A is a pictorial used to further describe an out-of-focus surface contribution received by a light sensor used in the optical tomography system of FIG. 1.

Referring now to FIGS. 7 and 7A, in which like elements of FIGS. 6-6C are shown having like reference designations, the aperture, A, is associated with the imagining system of FIG. 6. Here, the focal plane does not lie on a surface, S, of an object being imaged. Therefore, the surface, S, is substantially out of focus. Also, the in-focus point R is not on the surface, S, to be imaged.

From equation (0.3), the total collected power at the point, R', is equivalent to the total power radiated by the point, R, into the solid angle, $\Omega$, defined by point, R, and the area, A, of the aperture, A.

Figure 7B:
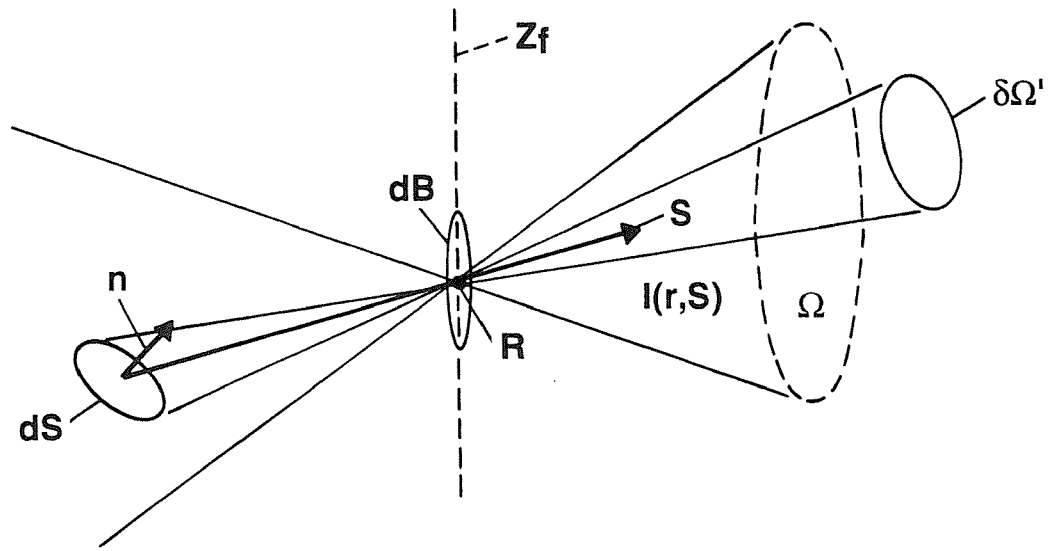
FIG. 7B is a pictorial used to describe an out-of-focus a solid angle contribution received by a light sensor used in the optical tomography system of FIG. 1.

Referring now to FIG. 7B, in which like elements of FIGS. 6-6C and 7 are shown having like reference designations, a differential surface area, dS, which is out of focus, contributes light energy to point, R'. It will be understood that all of the power that leaves the differential surface area, dS, and passes through the point, R, within the solid angle, $\Omega$, is detected at the point, R'. In order to simplify the calculations, the total power measured at the point, R' (FIG. 7), is equivalent to the power that traverses the differential surface area, dB, within the solid angle, $\Omega$. As described above, this virtual surface represents the image of the light sensor at the point, R'.

The contribution of the differential surface area, dS, can be calculated. It will be appreciated that the power radiated must equal the power received. That is, the differential surface area, dS, radiates a certain power into the differential solid angle, $\delta\Omega'$. From this differential radiation, only those values that fall within the solid angle, $\Omega$, will contribute to the total power. Therefore, the differential power measured at the point, R' (FIG. 7), due to the differential surface area, dS, may be written as:

$$dP(R) = \int_{\Omega'} I_f(R,s) m \cdot s \, dB d\Omega', \ \forall s \in \Omega \qquad (0.12)$$

where $I_f$ is the specific intensity at the focal plane, $Z_f$, the surface normal, m (not shown), is the surface normal of the differential surface area, dB, and the solid angle, $S\Omega'$, is defined by the differential surface area, dS, and the point, R.

Figure 7C:
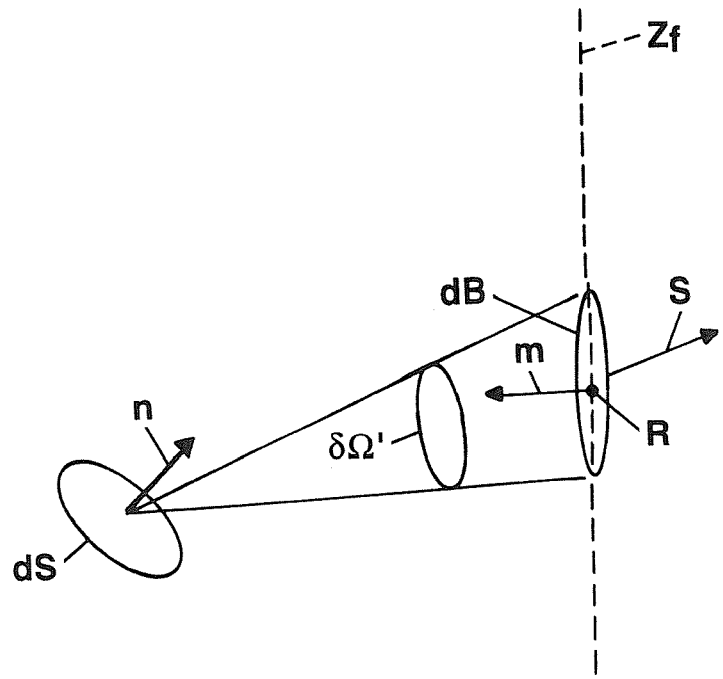
FIG. 7C is another pictorial used to describe an out-of-focus solid angle contribution received by a light sensor used in the optical tomography system of FIG. 1.

Referring now to FIG. 7C, in which like elements of FIGS. 6-6C and 7-7B are shown having like reference designations, another property of the specific intensity, invariance, provides that Equation (0.12) above can be written in terms of the specific intensity, $I(r,s)$, at the differential surface area, dS:

$$dP(R) = \int_{\Omega'} I(r,s) n \cdot s \, dS d\Omega', \ \forall s \in \Omega, \qquad (0.13)$$

where the solid angle, $S\Omega'$, is defined by the differential surface area, dB, and the point r is the surface point at which the differential surface area, dS, is located. It should be recognized that the only values of, s, that contribute to the solid angle integral in Equation (0.13) are those that fall within the solid angle, $\Omega$ (FIG. 7B). It should be appreciated that the above equation corresponds to the total power received at the point, R' (FIG. 7), due to a differential surface area, dS.

Figure 7D:
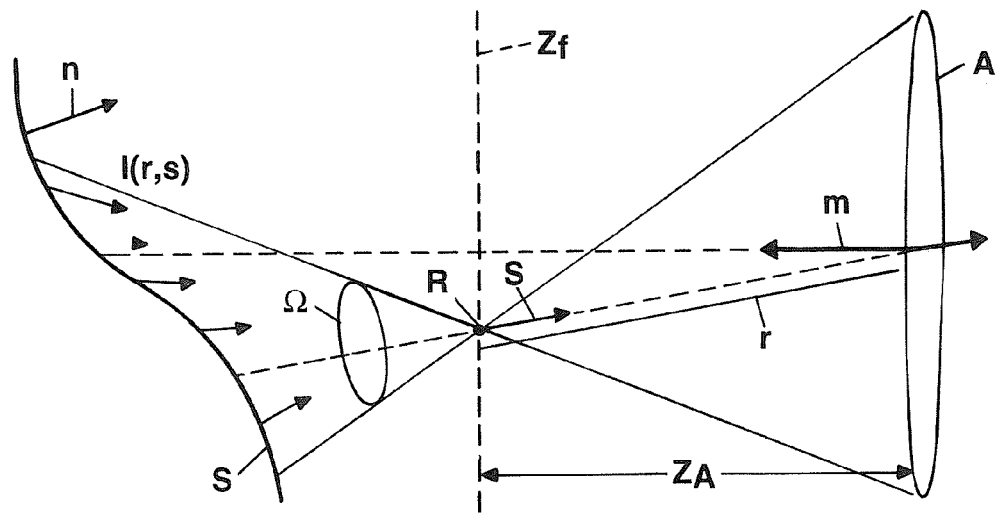
FIG. 7D is a pictorial used to describe an out-of-focus full surface contribution received by a light sensor used in the optical tomography system of FIG. 1.

Referring now to FIG. 7D, in which like elements of FIGS. 6-6C and 7-7C are shown having like reference designations the total power takes into account the complete surface, for those values that fall within the solid angle, $\Omega$ (FIGS. 7 and 7B) through the differential surface area, dB (FIG. 7B). This is schematically represented in FIG. 7D. The total power received at the point, R' (FIG. 7), is therefore:

$$P(R) = \int_S dP(R) = \int_S dS \int_{\Omega'} I(r,s) n \cdot s \, d\Omega', \ \forall s \in \Omega \qquad (0.14)$$

Figure 7E:
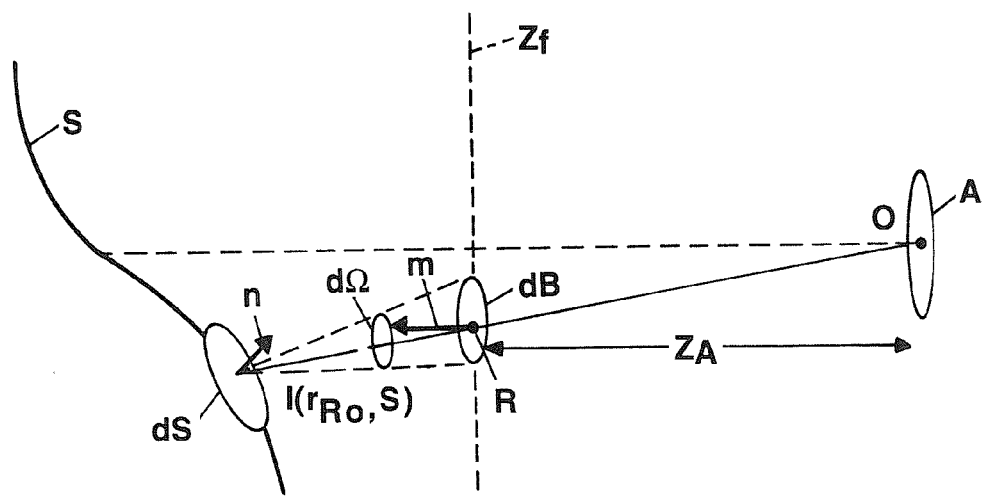
FIG. 7E is another pictorial used to describe an out-of-focus contribution received by a light sensor used in the optical tomography system of FIG. 1.

Referring now to FIG. 7E, in which like elements of FIGS. 6-6C and 7-7D are shown having like reference designations, for a small aperture, where $Z_A \gg R_A$, and an out of focus surface, S, it is convenient to return to the contribution of a single differential surface area, dS, given in Equation (0.13). Since the solid angle in this case is a delta function, we may rewrite Equation (0.13) as:

$$dP(R) = I(r,s) n \cdot s \delta(s - u_{r-O}) \delta(s - u_{O-R}) dS d\Omega', \qquad (0.15)$$

where the delta functions ensure that the direction of energy that passing through the points, R and O, is taken into account. Rewriting the solid angle, $d\Omega'$, in terms of the differential surface area, dB, we obtain:

$$dP(R) = I(r,s) n \cdot s \delta(s - u_{r-O}) \delta(s - u_{O-R}) dS \frac{m \cdot s \, dB}{|r - R|^2}, \qquad (0.16)$$

which is equivalent to:

$$dP(R) = I(r, u_{r-R}) \delta(u_{r-R} - u_{R-O})(u_{r-R} \cdot n)(u_{r-R} \cdot m) \frac{dS dB}{|r - R|^2} \qquad (0.17)$$

Introducing this expression into Equation (0.14) we obtain the total power received at the point, R', (FIG. 7) is:

$$P(R) = I(r_{RO}, u_{R-O})[u_{R-O} \cdot n(r_{RO})][u_{O-R} \cdot m] \frac{dS dB}{|r_{RO} - R|^2} \qquad (0.18)$$

where $r_{RO}$ is the point where the surface, S, and the line given by RO intersect. That is, from Equation (0.18) it is clear that in the case of a small aperture only one element of the surface, S, will contribute to the intensity at a certain pixel. What this represents is that for a very small aperture, A, all of surface, S, will be in focus. The differential surface area, dB, represents the image of the light sensor at the focal plane, $Z_f$.

For a large aperture, where $R_A \gg Z_A$, all surface points on the surface, S, contribute to the power measured at the point, R' (FIG. 7). Rewriting the solid angle in terms of the differential surface area, dB.

$$P(R) = \int_S I(r, u_{r-R})[n \cdot u_{r-R}][m \cdot u_{r-R}] \frac{dS dB}{|r - R|^2} \qquad (0.19)$$

That is, for all points out of focus, there is a complete de-blurring. Therefore, very large apertures have a very sharp focal plane, $Z_f$, or focus depth.

It should be recognized that for all of the expressions where $I(r,s)$ has not been defined explicitly, the above expression includes all high-order angular components of the light at the point, r (FIG. 7D). For an arbitrary surface, S, being imaged we may assume the transformation of a general point, $r_b$, (equivalent to point r) within the surface, S, and a light detector at a general point, $r_d$ (equivalent to point R) within the focal plane $Z_f$ as:

$$\Gamma(r_d, r_b) = \xi(r_b, r_d) f(n, m) dA_d,  \quad (0.20)$$

In Equation (0.20) n and m represent the surface normal, n, and the detector normal, m, respectively, as before. Function $\xi$ is a visibility factor that discards surface points not visible from the light sensor, whereas function $f$ includes the angles of acceptance of the aperture, A, with regards to each surface component, defined by n and m. Function $\Gamma(r_b, r_d)$ includes all the high-order angular contributions of light and may therefore be written as $$\Gamma(r_b, r_d) = \sum_n a_n \Gamma^{(n)}(r_b, r_d),$$

where $\Gamma^{(n)}(r_b, r_d)$ is the n-order angular contribution, i.e., a function of the n-order Legendre Polynomial, and $a_n$, is the contribution of this order.

Using Equation (0.20) we may relate a set of light intensities $U(r_s, r_b)$ at the diffuse/non-diffuse air-tissue interface delineated by the surface, S, to non-contact light intensity measurements $U_{nc}(r_s, r_d)$ obtained from a free-space light sensor at $r_d \notin V$, i.e., $$U_{nc}(r_s, r_d) = \sum_{r_b \in S} \Gamma(r_d, r_b) U(r_s, r_b) \Delta S  \quad (0.21)$$

where $\Gamma(r_b, r_d)$ is a matrix. In the case where there is a one to one correspondence (surface in focus), $\Gamma(r_b, r_d)$ will be a diagonal matrix. Equation (0.21) may also be envisaged as a convolution of the surface values with the transformation function $\Gamma(r_b, r_d)$.

The transformation of Equation (0.21) makes no assumptions regarding the position, orientation, or area of the surface elements or the light detectors but explicitly models these parameters through Equation (0.20).

As we consider a finite set of detectors and surface elements, Equation (0.21) can be rewritten as a matrix equation where $U_{nc} \in R^{|det|, |src|}$, $\Gamma \in R^{|det|, |S|}$ and $U \in R^{|S|, |src|}$ describe an imaging system with |det| detectors, |src| sources and |S| surface elements. Each matrix element (b, s) in U contains the average intensity on a surface element $r_b \in S$ created by a source $r_s$ as described by Equation (0.1). Transforming the volume integral into a sum of volume elements (voxels) of volume $\Delta V_r$ leads to:

$$U_{b,s} = \sum \Delta V_r \frac{U_0(r_s, r) G(r_b, r) \Gamma(r_b, r_d)}{U_0(r_s, r_b) \Gamma(r_b, r_d)} \frac{v}{D} c(r)  \quad (0.22)$$

where the sum is performed over all the elements within V.

Equation (0.22) can be considered to be the product of a matrix $W \in R^{|S|, |V|}$ with a vector $c \in R^{|V|}$, where the matrix contains all the factors in Equation (0.22) except for c. Thus, the complete discrete system can be written $U_{nc} = Wc$. As W tends to be very large, the inversion cannot be performed directly. Instead, iterative techniques, such as the algebraic reconstruction technique with randomized projection order (R-ART) can be used, conjugate minimization methods, or other methods.

All references cited herein are hereby incorporated herein by reference in their entirety.

Having described preferred embodiments of the invention, it will now become apparent to one of ordinary skill in the art that other embodiments incorporating their concepts may be used. It is felt therefore that these embodiments should not be limited to disclosed embodiments, but rather should be limited only by the spirit and scope of the appended claims.

What is claimed is:

1. A system for optical tomography of an object, the system comprising:
    one or more light sources configured to direct light into the object;
    one or more light detectors configured to detect light having traveled through the object and in free space about the object to the one or more detectors, wherein the one or more light detectors are disposed substantially opposite from a side of the object into which light is directed from the one or more light sources;
    a surface-capture system configured to generate a surface model of at least a portion of the surface of the object;
    a model processor configured to provide one or more optical models associated with the surface model, wherein the one or more optical models accounts for propagation of light in free space between the object and the one or more detectors; and
    a solution processor configured to process data corresponding to the detected light using the one or more optical models to provide a tomographic image of the object.

2. The system of claim 1, wherein the one or more light sources are configured to emit near infra-red (NIR) light to excite one or more fluorochromes within the object.

3. The system of claim 2, wherein the one or more light detectors are configured to detect fluorescent light emitted from the one or more fluorochromes within the object following excitation by the near infra-red light.

4. The system of claim 1, wherein the one or more light detectors are configured to be disposed more than one centimeter from the surface of the object.

5. The system of claim 4, wherein the one or more light detectors are configured to be disposed between 5 and 25 centimeters from the surface of the object.

6. The system of claim 1, wherein the object is a diffuse medium.

7. The system of claim 1, wherein the object is an animal.

8. A method for generating a tomographic image of an object, the method comprising:
    detecting, with a light detector, light having traveled through a non-homogeneous, diffuse object and in free space about the object to the detector following exposure of the object to light directed from a light source, wherein the light detector is disposed substantially opposite from a side of the object into which light is directed from the light source; and
    generating a tomographic image of the object using at least the following: (1) a measure of detected light having traveled through the object and in free space about the object to the detector; (2) a surface model of at least a portion of a surface of the object; and (3) a model of light propagation that accounts for propagation of light in free space between the object and the detector.

9. The method of claim 8, wherein the detected light comprises fluorescent light emitted from one or more fluorochromes within the object.

10. The method of claim 9, wherein the light source directs near infra-red (NIR) light into the object and the detected light comprises fluorescent light emitted from the one or more fluorochromes within the object following excitation by the near infra-red light.

11. The method of claim 8, further comprising the step of displaying the tomographic image.

12. The method of claim 8, wherein the light detector is disposed more than 1 centimeter from the surface of the object.

13. The method of claim 12, wherein the light detector is disposed between 5 and 25 centimeters from the surface of the object.

14. The method of claim 8, wherein the object is a diffuse medium.

15. The method of claim 8, wherein the object is an animal.

* * * * *

UNITED STATES PATENT AND TRADEMARK OFFICE
CERTIFICATE OF CORRECTION

PATENT NO. : 8,326,406 B2
APPLICATION NO. : 13/099929
DATED : December 4, 2012
INVENTOR(S) : Vasilis Ntziachristos et al.

It is certified that error appears in the above-identified patent and that said Letters Patent is hereby corrected as shown below:

On the Title Page

Abstract, line 4 delete "and" and replace with -- an --.

In the Specification

Column 15, line 50 delete " $R'|_{z=z_f} \leftrightarrow MR|_{z=z_f}$ " and replace with -- $R'|_{z=z_i} \leftrightarrow MR|_{z=z_f}, M$ --.

Column 19, line 43 delete "SΩ'" and replace with -- δΩ' --.

Column 19, line 55 delete "SΩ'" and replace with -- δΩ --.

Column 21, line 46 delete "ΓÅR" and replace with -- ΓεR --.

Signed and Sealed this
Fifth Day of May, 2015

Michelle K. Lee
*Director of the United States Patent and Trademark Office*